(12) United States Patent
Nativ et al.

(10) Patent No.: US 10,993,759 B2
(45) Date of Patent: May 4, 2021

(54) HYPOTHERMIC LINEAR SURGICAL STAPLERS AND METHODS OF USE

(71) Applicant: Ethicon, Inc., Somerville, NJ (US)

(72) Inventors: Nir I. Nativ, West Orange, NJ (US); Leo B. Kriksunov, Ithaca, NY (US); Robert J. Tannhauser, Bridgewater, NJ (US); Silvia Chen, Kendall Park, NJ (US)

(73) Assignee: Ethicon, Inc., Somerville, NJ (US)

( * ) Notice: Subject to any disclaimer, the term of this patent is extended or adjusted under 35 U.S.C. 154(b) by 231 days.

(21) Appl. No.: 15/789,094

(22) Filed: Oct. 20, 2017

(65) Prior Publication Data

US 2019/0117287 A1    Apr. 25, 2019

(51) Int. Cl.
| | | |
|---|---|---|
| A61B 18/02 | (2006.01) | |
| A61B 17/072 | (2006.01) | |
| A61F 7/00 | (2006.01) | |
| A61B 90/00 | (2016.01) | |
| A61B 18/00 | (2006.01) | |
| A61B 17/00 | (2006.01) | |

(52) U.S. Cl.
CPC ........ *A61B 18/02* (2013.01); *A61B 17/07207* (2013.01); *A61F 7/00* (2013.01); *A61B 2017/00092* (2013.01); *A61B 2017/07257* (2013.01); *A61B 2017/07271* (2013.01); *A61B 2017/07285* (2013.01); *A61B 2018/00023* (2013.01); *A61B 2018/00047* (2013.01); *A61B 2018/00095* (2013.01); *A61B 2018/0225* (2013.01); *A61B 2090/0807* (2016.02); *A61F 2007/0087* (2013.01)

(58) Field of Classification Search
CPC .............. A61B 17/0684; A61B 17/072; A61B 17/1155; A61B 17/10; A61B 18/1445; A61B 2017/00092; A61B 2017/07257; A61B 2017/07271; A61B 2018/00011; A61B 2018/00023; A61B 2018/00047; A61B 2018/00791; A61B 34/70; A61F 7/12; A61F 200/0056; A61F 200/0057; A61F 200/0075; A61F 200/0096; A61F 200/126

USPC ....................................... 227/176.1
See application file for complete search history.

(56) References Cited

U.S. PATENT DOCUMENTS

| | | |
|---|---|---|
| 3,794,039 A | 2/1974 | Kollner et al. |
| 4,281,785 A | 8/1981 | Brooks |
| 4,805,823 A | 2/1989 | Rothfuss |
| 5,173,133 A | 12/1992 | Morin et al. |
| 5,211,646 A | 5/1993 | Alperovich et al. |

(Continued)

OTHER PUBLICATIONS

International Search Report and Written Opinion for the Application No. PCT/US2018/055858, dated Jan. 30, 2019, pp. 15.

*Primary Examiner* — Chelsea E Stinson
*Assistant Examiner* — Himchan Song
(74) *Attorney, Agent, or Firm* — David R. Crichton; Leo B. Kriksunov

(57) ABSTRACT

The present invention relates to surgical instruments and methods for enhancing properties of tissue repaired or joined by surgical staples and, more particularly to surgical instruments and methods designed to enhance the properties of repaired or adjoined tissue at a target surgical site. The present invention further relates to hypothermic linear stapling instruments configured to pre-cool the tissues being joined by staples.

8 Claims, 18 Drawing Sheets

(56) References Cited

U.S. PATENT DOCUMENTS

| | | | |
|---|---|---|---|
| 5,275,323 A | 1/1994 | Schulze et al. | |
| 5,415,334 A | 5/1995 | Williamson, IV et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,807,393 A | 9/1998 | Williamson, IV et al. | |
| 5,814,055 A | 9/1998 | Knodel et al. | |
| 5,906,625 A * | 5/1999 | Bito | A61B 17/122 606/139 |
| 6,656,177 B2 | 12/2003 | Truckai et al. | |
| 6,694,984 B2 | 2/2004 | Habib | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,169,146 B2 | 1/2007 | Truckai et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | Mckenna et al. | |
| 7,762,445 B2 | 7/2010 | Heinrich et al. | |
| 7,815,641 B2 | 10/2010 | Dodde et al. | |
| 8,408,439 B2 | 4/2013 | Huang et al. | |
| 8,453,914 B2 | 6/2013 | Laurent et al. | |
| 8,647,336 B2 * | 2/2014 | Werneth | A61B 18/02 606/23 |
| 8,679,114 B2 | 3/2014 | Chapman et al. | |
| 8,715,277 B2 | 5/2014 | Weizman | |
| 8,911,486 B1 | 12/2014 | Drnek et al. | |
| 9,005,199 B2 | 4/2015 | Beckman et al. | |
| 9,044,261 B2 * | 6/2015 | Houser | A61B 17/29 |
| 9,186,142 B2 | 11/2015 | Fanelli et al. | |
| 9,259,265 B2 | 2/2016 | Harris et al. | |
| 9,295,514 B2 | 3/2016 | Shelton, IV et al. | |
| 10,004,552 B1 * | 6/2018 | Kleyman | A61B 18/085 |
| 2002/0022829 A1 * | 2/2002 | Nagase | A61B 18/20 606/12 |
| 2002/0032440 A1 * | 3/2002 | Hooven | A61B 18/1445 606/41 |
| 2003/0024538 A1 * | 2/2003 | Edwards | A61B 18/1492 128/898 |
| 2007/0135803 A1 * | 6/2007 | Belson | A61B 5/064 606/1 |
| 2007/0262116 A1 * | 11/2007 | Hueil | B25C 5/0292 227/175.1 |
| 2009/0048589 A1 * | 2/2009 | Takashino | A61B 18/1445 606/28 |
| 2011/0306967 A1 * | 12/2011 | Payne | A61B 18/1445 606/41 |
| 2012/0053577 A1 * | 3/2012 | Lee | A61B 18/1815 606/33 |
| 2012/0089047 A1 * | 4/2012 | Ryba | A61B 18/02 600/554 |
| 2014/0046411 A1 * | 2/2014 | Elkins | A61F 7/0085 607/104 |
| 2014/0094790 A1 * | 4/2014 | Hafner | A61B 18/1482 606/33 |
| 2014/0180281 A1 * | 6/2014 | Rusin | A61B 34/76 606/45 |
| 2014/0371735 A1 | 12/2014 | Long | |
| 2015/0374373 A1 | 12/2015 | Rector et al. | |
| 2016/0120601 A1 | 5/2016 | Boudreaux et al. | |
| 2017/0112560 A1 * | 4/2017 | Ross | A61B 18/1445 |
| 2017/0165105 A1 * | 6/2017 | Anderson | A61N 5/0616 |
| 2019/0200977 A1 * | 7/2019 | Shelton, IV | A61B 17/07207 |

* cited by examiner

HYPOTHERMIC LINEAR SURGICAL STAPLERS AND METHODS OF USE

FIELD OF THE INVENTION

The present invention relates to surgical instruments and methods for enhancing properties of tissue repaired or joined by surgical staples and, more particularly to surgical instruments and methods designed to pre-cool the tissues being joined by staples to improve outcomes for the repaired or adjoined tissue at a target surgical site.

BACKGROUND OF THE INVENTION

The medical field has utilized various techniques to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples have been used in certain situations to replace suturing thread when joining or anastomosing various body structures, such as, for example, the bowel. The surgical stapling devices employed to apply staples are generally designed to simultaneously cut and seal an extended segment of tissue in a patient.

Linear or annular/circular surgical stapling devices are employed by surgeons to sequentially or simultaneously apply one or more rows of surgical fasteners, e.g., staples, to body tissue to join segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Many surgical staplers for use in open and endoscopic procedures are known. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While many of the surgical staplers referred to above are used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to cut and close a vessel leading to a lung. For instance, the vessels leading to an organ may be severed and closed by a stapler before removal of the organ from the thoracic cavity. Surgical staplers may be used in various other settings and procedures. Examples of surgical staplers that may be particularly suited or use through a thoracotomy are disclosed in U.S. Pat. No. 9,186,142, entitled "Surgical Instrument End Effector Articulation Drive with Pinion and Opposing Racks", the disclosure of which is incorporated by reference herein.

Annular or circular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

U.S. Pat. No. 5,173,133 "METHOD FOR ANNEALING STAPLER ANVILS" discloses a method for annealing a delimited portion of an anvil member for use in a surgical stapler, said method comprising: a) providing a means for heating; b) placing said anvil member in cradle means, said cradle means comprising a member fabricated from a thermally conductive material and possessing means configured and dimensioned to receive said anvil such that a first part of the exterior surface of the anvil is in thermally conductive contact with the interior surface of the receiving means and a second part of the exterior surface of the anvil is exposed; c) positioning said cradle in proximity to said heating means such that the delimited portion of the second part of the exterior surface of the anvil member is within the heating range of said heating means; and d) operating said heating means such that the delimited exposed portion of the anvil member is heated to an annealing temperature.

U.S. Pat. No. 9,005,199 "Heat management configurations for controlling heat dissipation from electrosurgical instruments" discloses a surgical instrument, comprising: an end effector comprising: a first jaw comprising an electrode having a distal end; a second jaw, wherein the first jaw and the second jaw are operably coupled together; and a cutting member configured to translate between a retracted position and a fully advanced position with respect to the first jaw, wherein the cutting member comprises a cutting surface and a body, wherein the body defines a cavity and at least one opening communicating with the cavity, and wherein the at least one cutting member opening is proximal to the distal end of the electrode when the cutting member is in the fully advanced position.

U.S. Pat. No. 8,679,114 "Incorporating rapid cooling in tissue fusion heating processes" discloses an electrode sealing assembly designed for use with an electrosurgical instrument for sealing tissue, comprising: first and second jaw members movable from a first position in spaced relation relative to one another to at least one second position for grasping tissue therebetween, the jaw members including: electrically conductive sealing plates disposed in opposing relation to one another, at least one jaw member including: a thermoelectric cooling plate having a first surface in direct contact with an outer surface of the sealing plate, the thermoelectric cooling plate including first and second electrical connections disposed on opposite sides of the thermoelectric cooling plate, the first connection configured to selectively transmit a first electrical potential and the second connection configured to selectively transmit a second electrical potential such that heat generated by the sealing plates is transferred away from the tissue via the thermoelectric cooling plate, wherein the electrically conductive seal plates each include inward lateral side edges, the inward lateral side edges and the first surface of the thermoelectric cooling plate configured to form a knife slot therebetween dimensioned to receive a knife blade therein, the knife blade disposed substantially adjacent and in proximity to the thermoelectric cooling plate to enable heat transfer from the knife blade to the thermoelectric cooling plate, and wherein the at least one jaw member further includes a first heat sink disposed in contact with a second surface of the thermoelectric cooling plate, the first heat sink made from a thermally conductive, electrically insulative cool polymer.

U.S. Pat. No. 7,815,641 "Surgical instrument and method for use thereof" discloses a surgical instrument for treating a tissue, comprising: a hand piece; and a tissue engaging portion arranged to be received by the hand piece, the tissue engaging portion comprising first and second opposed jaw members having an open position and a closed position for engaging the tissue therebetween, the first and second jaw members arranged to receive surgical energy from a surgical generator, and at least one cooling member spaced from at least one of the first and second jaw members, the at least one cooling member separately movable with respect to the jaw members and having an open position and a closed position for engaging the tissue, wherein positioning the jaw members in their closed position and applying surgical energy to the tissue allows for treatment of the tissue, and positioning the at least one cooling member in its closed position provides at least one of a pressure gradient or a thermal gradient between the jaw members and the at least one cooling member.

U.S. Patent Application Publication No. 2014/0180281 "ELECTRIC STAPLER DEVICE" discloses an end effector assembly of a forceps, comprising: first and second jaw members, at least one of the jaw members moveable relative to the other between a spaced-apart position and an approximated position for grasping tissue therebetween, each jaw member including: a plurality of spaced apart seal plates, wherein each seal plate corresponds to a seal plate on the opposite jaw member to form a pair of seal plates, each pair of seal plates is individually activatable; and a cutting element, wherein when the first and second jaw members are in the approximated position, the pairs of seal plates closer to the cutting element define a gap therebetween that is smaller than the gap between pairs of seal plates further from the cutting element.

U.S. Pat. No. 4,281,785 "Stapling apparatus and method and thermoplastic staples used therewith" discloses a stapling apparatus for stapling an assembly of components, said apparatus having a stapling head for carrying and serially dispensing a plurality of staples made entirely of thermoplastic material, each of said staples comprising a bight and a pair of legs extending in substantially parallel relation from opposite ends of said bight, staple driving means in said head for driving each of said staples through said assembly once each staple is dispensed into a driving position, and a clinching anvil for clinching outer portions of said legs of each staple, the improvement wherein said anvil has a heated portion comprising an integral heater for heat shaping said outer portions of said legs in clinched relation after disposal of said legs through said assembly and a cooled portion comprising an integral cooling device for cooling said outer portions of said legs after shaping thereof, and said apparatus comprising a single support for said anvil and its heated and cooled portions, said support being mounted for pivoting movements about a single pivot to enable movement of said heated portion into position to provide said heat shaping of said outer portions and then movement of said cooled portion into position to provide said cooling of said outer portions.

U.S. Pat. No. 7,169,146 "Electrosurgical probe and method of use" discloses an electrosurgical instrument for delivering energy to tissue, comprising: a working end for engaging the tissue; a surface layer at an exterior portion of the working end, the surface layer comprising a matrix of polymeric PTC composition adapted to deliver electrical current to the tissue; and a cooling structure at an interior portion of the working end; wherein the cooling structure cools the PTC matrix to lower the temperature of one or more portions of the PTC matrix.

U.S. Pat. No. 3,794,039 "APPARATUS FOR CRYOSURGERY" discloses an apparatus for cryosurgery having a central unit containing a supply of liquid cryogenic coolant, control and regulating means, and sub atmospheric suction means connected to a probe for freezing tissue, the improvement comprising: a. a cryogenic probe including a grip member having a hollow cryogenic coolant feed line supported by said grip member, said line being open at the tip thereof and connected at one end to said cryogenic coolant supply for transmitting liquid coolant to impinge directly upon tissue to be frozen; b. a hollow cryogenic coolant return line open at a transparent end thereof concentrically disposed around said feed line to form a space therebetween; and c. means communicating said space to said sub atmospheric suction means for returning vaporized coolant from said feed line, the open end of said feed line being recessed with respect to the corresponding open end of said return line.

U.S. Pat. No. 6,656,177 "Electrosurgical systems and techniques for sealing tissue" discloses a jaw assembly of a surgical instrument, comprising: an instrument working end carrying first and second jaws actuable between a first open position and a second closed position, the jaws in the closed position defining a longitudinal axis and wherein the jaws further define exterior faces and interior jaw faces having a longitudinal length; an axially extending member that is actuable from a first retracted position to a second extended position in an axial channel extending the length of the exterior and interior jaw faces; and wherein said axially extending member defines first cam surface portions that engage cooperating second cam surface portion that extend the entire length of the interior jaw faces to actuate the jaws toward the closed position and prevent flexing apart of said jaws.

U.S. Pat. No. 6,694,984 "Liver surgery" discloses a method of reducing blood loss during liver surgery, wherein diseased or damaged tissue is removed from the liver by delivery of thermal energy to the tissue by a probe, wherein the method is carried out to define liver resection with an at least 2 cm wide coagulative necrosis zone in surgery the improvement comprising: a multiprobe application followed by a scalpel division of the parenchyma and suture of blood vessels bigger than about 2.5 mm.

U.S. Patent Application Publication No. 2014/0371735 "ELECTROSURGICAL INSTRUMENT END EFFECTOR WITH PREHEATING ELEMENT" discloses an apparatus for operating on tissue, wherein the apparatus comprises an end effector, the end effector comprising: (a) a first jaw; (b) a second jaw, wherein the first jaw is selectively pivotable toward and away from the second jaw to capture tissue; (c) at least one preheating element, wherein the at least one preheating element is disposed within one or both of the first jaw or the second jaw, wherein the at least one preheating element is operable to heat up and thereby transfer heat to tissue captured between the first jaw and the second jaw through; and (d) at least one electrode, wherein the at least one electrode is operable to apply RF energy to tissue captured between the first jaw and the second jaw.

U.S. Patent Application Publication No. 2016/0120601 "ELECTROSURGICAL INSTRUMENT WITH SENSOR" discloses an apparatus for operating on tissue, the apparatus comprising: (a) a body; (b) a shaft extending distally from the body; (c) an end effector configured to receive energy from an energy source, wherein the end effector comprises: (i) a first jaw, and (ii) a second jaw, wherein the second jaw is pivotable relative to the first jaw to transition the end effector from an open configuration to a closed configuration, wherein the first jaw and second jaw define a closure gap between each other when the end effector is in the closed configuration; and (d) a sensor, wherein the sensor is operable to detect when the end effector is in the closed configuration, wherein the sensor is in communication with the energy source, wherein the sensor is operable to communicate a signal to the energy source when the sensor detects the end effector in the closed configuration.

U.S. Pat. No. 7,762,445 "Electrosurgical stapling apparatus" discloses a surgical stapler, comprising: an anvil member having a plurality of staple-forming recesses defined therein for deforming a corresponding plurality of surgical staples, the anvil includes an electrically insulative material disposed on a tissue contacting surface thereof, wherein at least one of the plurality of staple-forming recesses is coated with the electrically insulative material, wherein the electrically insulative material is selectively removable, and wherein the electrically insulative material is selectively removed from the tissue contacting surface of the anvil member during a firing of the surgical stapler; a cartridge assembly including a staple cartridge defining a tissue contact surface and configured to retain a plurality of electrically conductive surgical staples; an electrical conduit adapted for connection to a surgical generator; and an actuator operatively connected to the cartridge assembly for deploying the plurality of surgical staples from the staple cartridge against the anvil member, the actuator being movable within the cartridge assembly and coupled to the electrical conduit, the actuator including an electrically conductive actuation sled and an electrically conductive knife blade, wherein the electrical conduit is configured for transmitting a thermogenic energy to the knife blade and to the staples through the actuation sled.

U.S. Pat. No. 5,807,393 "Surgical tissue treating device with locking mechanism" discloses a surgical instrument comprising: a tissue treating portion including: a therapeutic energy delivering device arranged to deliver therapeutic energy to tissue, and a tissue manipulation device; a shaft coupled to said tissue treating portion, said shaft including a therapeutic energy communication device operatively coupled to said therapeutic energy delivering device said energy delivering device and said energy communication device adapted to be actuated to deliver therapeutic energy to tissue; a tissue manipulation actuating device having a locked position and an unlocked position, said tissue manipulation actuating device extending through said shaft and operatively coupled to said tissue manipulation device; a locking mechanism coupled to said tissue manipulation actuating device for moving said tissue manipulation actuating device from said locked position to said unlocked position after said therapeutic energy delivering device and said therapeutic energy communication device are actuated to deliver therapeutic energy to tissue; a tissue parameter measurement and instrument control device adapted to provide a feedback signal representative of a tissue treatment status of tissue being treated by said therapeutic energy delivering device, said parameter measurement and instrument control device coupled to said tissue treating portion of said instrument; and a status indicator coupled to said parameter measurement and instrument control device, said status indicator arranged to provide a user perceptible signal indicating a tissue treatment status.

U.S. Pat. No. 8,715,277 "Control of jaw compression in surgical instrument having end effector with opposing jaw members" discloses a surgical instrument comprising: an end effector comprising a distal end and a proximate end, wherein the end effector comprises: a first jaw member comprising a distal end and a proximate end, wherein the proximate end of the first jaw member comprises a pin; a second jaw member opposing the first jaw member, wherein the second jaw comprises a distal end and a proximate end, wherein the proximate end of the second jaw member comprises a multi-lobed cam slot with at least three lobes, wherein the pin of the first jaw member is disposed and moveable within the multi-lobed cam slot between the three lobes, wherein the first jaw member is moveable relative to the second jaw member such that the first and second jaw members are transitionable between an open position and a closed position, such that the first and second jaw members are in the open position when the pin of the first jaw member is in a first lobe of the multi-lobed cam slot and the first and second jaw members are in the closed position when the pin of the first jaw member is in a second lobe of the multi-lobed cam slot, and wherein the pin of the first jaw member moves into a third lobe of the multi-lobed cam slot when the pin transitions from the first lobe to the second lobe; and a latch at a distal end of the end effector for latching the distal end of the first jaw member to the distal end of the second jaw member when the first and second jaw members are in the closed position.

U.S. Pat. No. 9,259,265 "Surgical instruments for tensioning tissue" discloses an end-effector configured to be attached to a surgical instrument comprising a closure beam, the end-effector comprising: a first jaw comprising an electrode; a second jaw, wherein at least one of the first jaw and the second jaw is movable relative to the other jaw between an open position and a closed position, and wherein, in the closed position, a first region of tissue is configured to be positioned intermediate the first jaw and the second jaw and is configured to be compressed; the first jaw comprising: a first slider member movably attached to the first jaw and movable relative to the electrode and to the closure beam, wherein the first slider member comprises a first tissue-contacting surface configured to engage a second region of tissue; and the second jaw comprising: a second slider member movably attached to the second jaw and movable relative to the electrode and to the closure beam, wherein the second slider member comprises a second tissue-contacting surface configured to engage the second region of tissue; a longitudinal slot; and a cutting member slidable within the longitudinal slot; wherein the first slider member and the second slider member are configured to change the width of the end effector and apply a tensile stretching force to tissue positioned intermediate the first region of tissue and the second region of tissue when the first slider member and the second slider member are moved laterally relative to the electrode and to the longitudinal slot.

U.S. Pat. No. 8,911,486 "Implantable devices for thermal therapy and related methods" discloses a method of applying thermal therapy to tissue, comprising: forming a tissue opening in a patient to access a target site within the patient; passing a thermal device through the tissue opening; placing the thermal device at the target site; closing the tissue opening with the thermal device at the target site; after closing the tissue opening, applying or continuing to apply thermal therapy to the target site through the thermal device; and after closing the tissue opening, pulling a tether attached to the thermal device to remove the thermal device from the patient without reopening the tissue opening; wherein the thermal device comprises a malleable pad.

U.S. Pat. No. 9,295,514 "Surgical devices with close quarter articulation features" discloses an apparatus, comprising: a shaft section extending longitudinally along a first plane; an end effector comprising a first jaw and a second jaw configured to pivotally open and close in a second plane relative to the first plane about a pivot point, wherein the first plane is orthogonal to the second plane; an articulation section disposed between the shaft section and the end effector, the articulation section configured to articulate in the second plane relative to the first plane in response to a rotatable articulation control mechanism, the articulation section comprising a molded member that defines at least one slot and at least one recess; the at least one slot comprising a first slot extending longitudinally along the length of the molded member, the first slot comprising an opening at one side of the molded member and terminating within the molded member on another side; a longitudinally slidable blade comprising an upper flange and a lower flange; a flexible firing element comprising upper and lower flexible bands slidably positioned within the at least one slot, the upper flexible band connected to the upper flange of the blade and the lower flexible band connected to the lower flange of the blade; wherein at least one of the first and second jaws comprises an electrode.

U.S. Pat. No. 5,211,646 "Cryogenic scalpel" discloses a cryogenic scalpel for conducting surgical operations on parenchymatous biological tissues, comprising: a hollow housing having an interior space; a working portion connected to said hollow housing and having a body extending in a lengthwise direction; heat-exchanger means for establishing a zone for cooling biological tissues during surgery by supplying cooling fluid to said interior space; a blade having two ends and a cutting lip, said ends of said blade being secured to said heat-exchanger means; a coolant free to circulate through said heat-exchanger means; a piping accommodated in said interior space of said hollow housing and communicating with said heat-exchanger means; a source of electromechanical oscillations accommodated in said hollow housing to establish reciprocating motion to said working portion with a frequency of electromechanical oscillation with the result that heating of said blade is precluded and parenchymatous biological tissues are separated by simultaneously cooling in said cooling zone created by said heat-exchanger means; and means for imparting electromechanical oscillations to said working portion so as to transmit reciprocating motion to said blade; said means for imparting being connected between said source of electromagnetic oscillations and said blade.

There is a need to improve the viability of the tissues being joined by staples and the viability of the resulting joint, to improve healing and prevent tissue necrosis and leaks.

SUMMARY OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when stapling tissue section to improve tissue viability under hypoxia conditions, prevent tissue inflammation, and to prevent leakage. The present invention further relates to hypothermic linear stapling instruments configured to pre-cool the tissues being joined by staples.

The present invention, in one aspect, relates to a hypothermic linear surgical stapler for stapling and optionally resecting at least one tissue comprising: a body, a shaft assembly, and an end effector, wherein the end effector comprises a lower jaw configured to receive a staple cartridge, an anvil pivotable toward and away from the lower jaw, and a translatable knife member; a disposable cartridge installed in the lower jaw, said cartridge containing a plurality of deployable staples in arrays separated by a tissue resection channel through which the knife member can translate; said anvil having on a tissue facing surface a plurality of staple forming pockets aligned with said deployable staples; wherein the anvil comprises at least one cooled zone located on the anvil or inside the anvil.

The cooled zone can be a reservoir or compartment filled with a coolant, wherein said coolant could be a fluid having a high heat capacitance. The coolant can be at least partially frozen or a combination of a frozen coolant and a melted coolant. On a compositional basis, the coolant can be, in whole or part, water, alcohol, glycerol, ethylene glycol or mixtures thereof. In one compositional embodiment, the coolant can be a glycerol-water mixture having melting point above 0° C. but below 8° C. In another embodiment, the coolant can be an instant coolant. In one compositional embodiment, the coolant can be ethanol, methanol, or ethanol-water mixture.

The reservoir can in one alternative be connected to a recirculation pump and a chiller via a supply channel and a drain channel. In still further embodiments, the cooled zone can include a Peltier element or be a cooled zone with compressed gas-cooled throttling orifices connected to gas conduits and to a source of compressed gas. In a still further embodiment, the cooled zone can include a heat pipe configured to transfer thermal energy between the anvil and a cooling zone in a stapler handle. A thermally conductive zone can extend from being in contact with the reservoir towards the anvil tissue facing surface. Optionally, the reservoir can have at least one window to enable visualization of the one or more coolants contained therein.

The present invention also relates to methods stapling tissue comprising the steps of:
 a) inserting the staple cartridge into the lower jaw;
 b) capturing the tissue between the anvil and the staple cartridge;
 c) cooling the tissue through conductive heat transfer between the tissue and the cooled zone while the tissue is captured between the anvil and the staple cartridge;
 d) translating the knife member distally from a proximal position to a distal position substantially simultaneously cutting the captured tissue forming a resected tissue edge and driving the plurality of staples of the staple cartridge through the captured tissue;
 e) optionally continuing cooling the stapled tissue;
 f) removing said surgical stapler from contact with tissue.

In various embodiments, the cooled zone is pre-cooled or frozen prior to steps a) or b) or c).

DETAILED DESCRIPTION OF THE INVENTION

Surgery often involves joining of two or more layers of tissue together with optional simultaneous sectioning of a portion of the tissue along the staple line. Typical surgical stapling instruments, such as surgical linear stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component. For linear surgical staplers, a disposable stapling cartridge is the staple-containing component, the cartridge typically installed in a jaw of the device, such as in a lower jaw adapted to hold the cartridge, and the opposing or upper jaw is the anvil component. The cartridge has a slot disposed between adjacent, parallel rows of staples and extending substantially the entire length of the rows of staples. The stapler includes firing means for the staples and a cutting means that is movable along the slot.

Referring now to FIGS. 1-6, a surgical stapling instrument or stapler is shown, with the figures taken from the U.S. Patent Publication No. 2015/0374373A1 "METHOD OF USING LOCKOUT FEATURES FOR SURGICAL STAPLER CARTRIDGE" which is incorporated by reference herein in its entirety.

Figure 1:
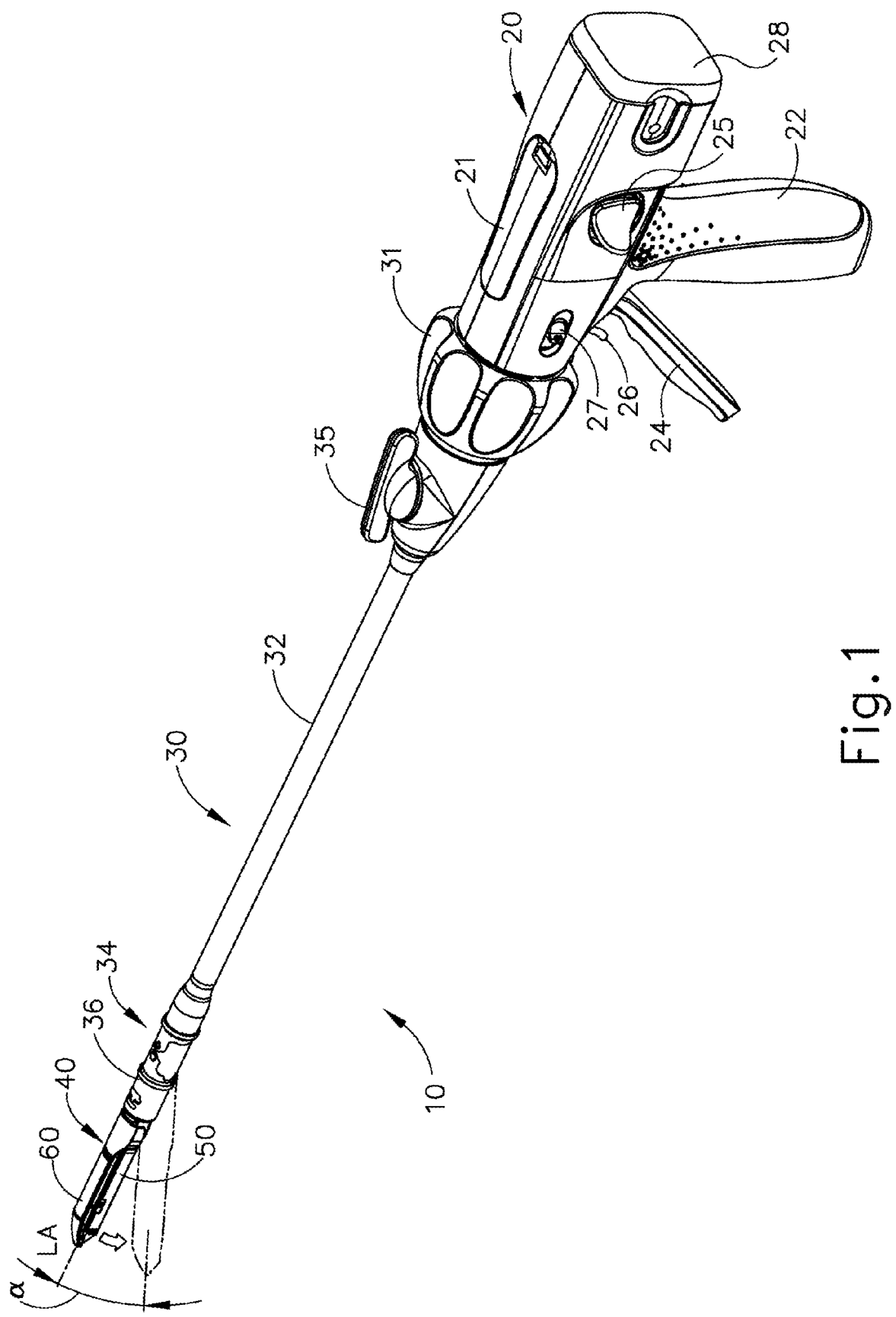
FIG. 1 depicts a perspective view of an exemplary articulating surgical stapling instrument.

FIG. 1 depicts an exemplary surgical stapling and cutting instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. Terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

Figure 2:
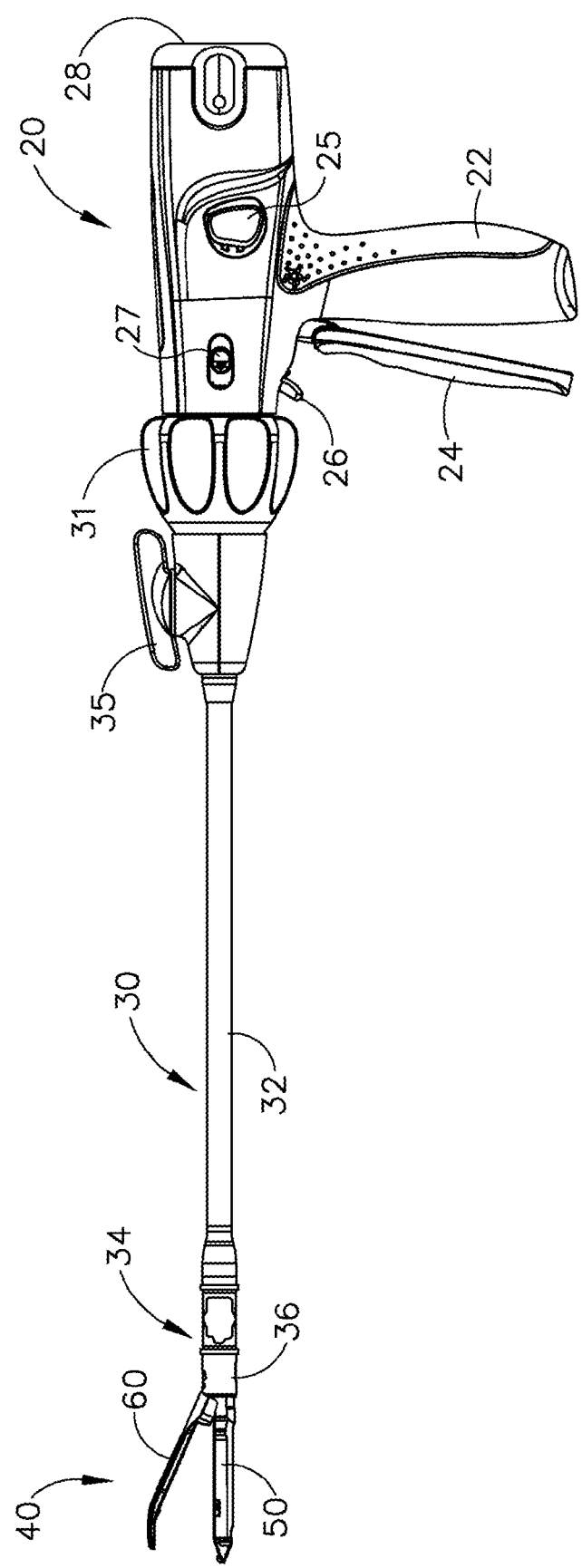
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22). Handle assembly (20) further includes an anvil release button (25), a firing beam reverse switch (27), and a removable battery pack (28). Handle assembly (20) may have a variety of other components, features, and operabilities, in addition to or in lieu of any of those noted above.

Figure 3:
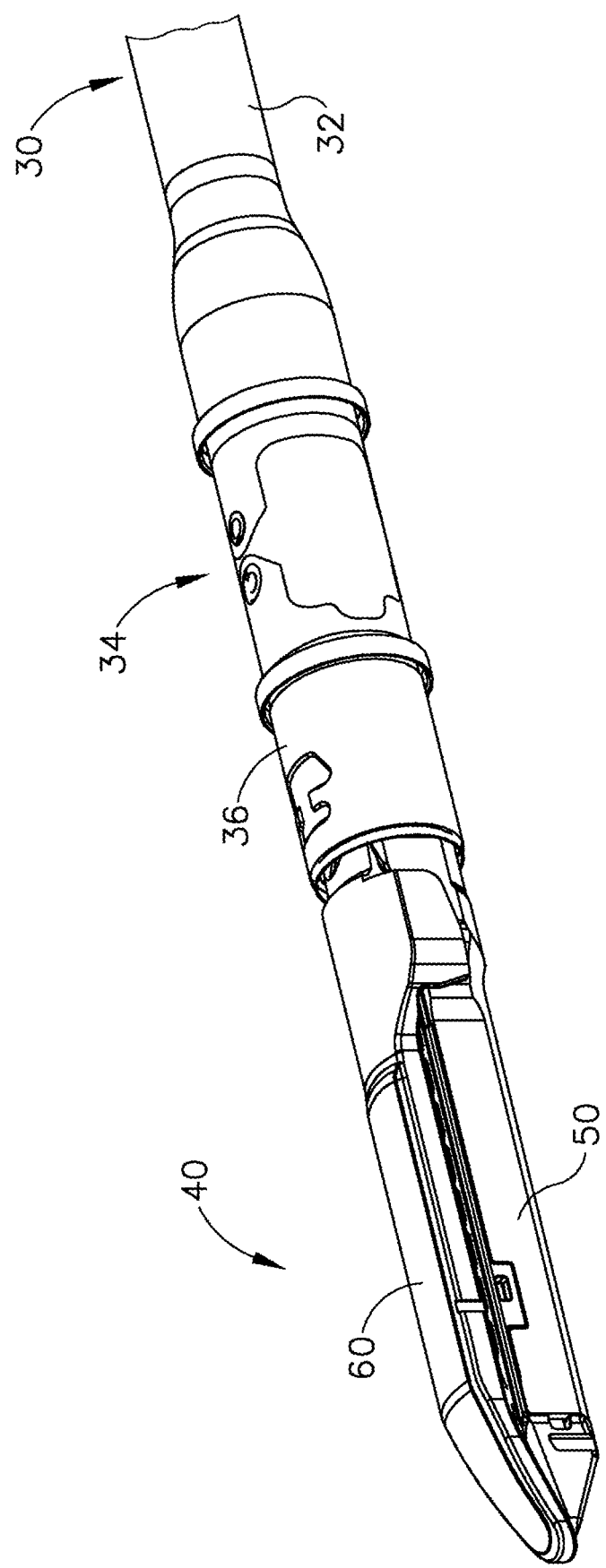
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34).

Articulation section (34) is operable to laterally deflect closure ring (36) and end effector (40) laterally away from the longitudinal axis (LA) of shaft assembly (30) at a desired angle (a). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3). As seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40).

As seen in FIGS. 4-7, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). Staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70).

The configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72).

Figure 4:
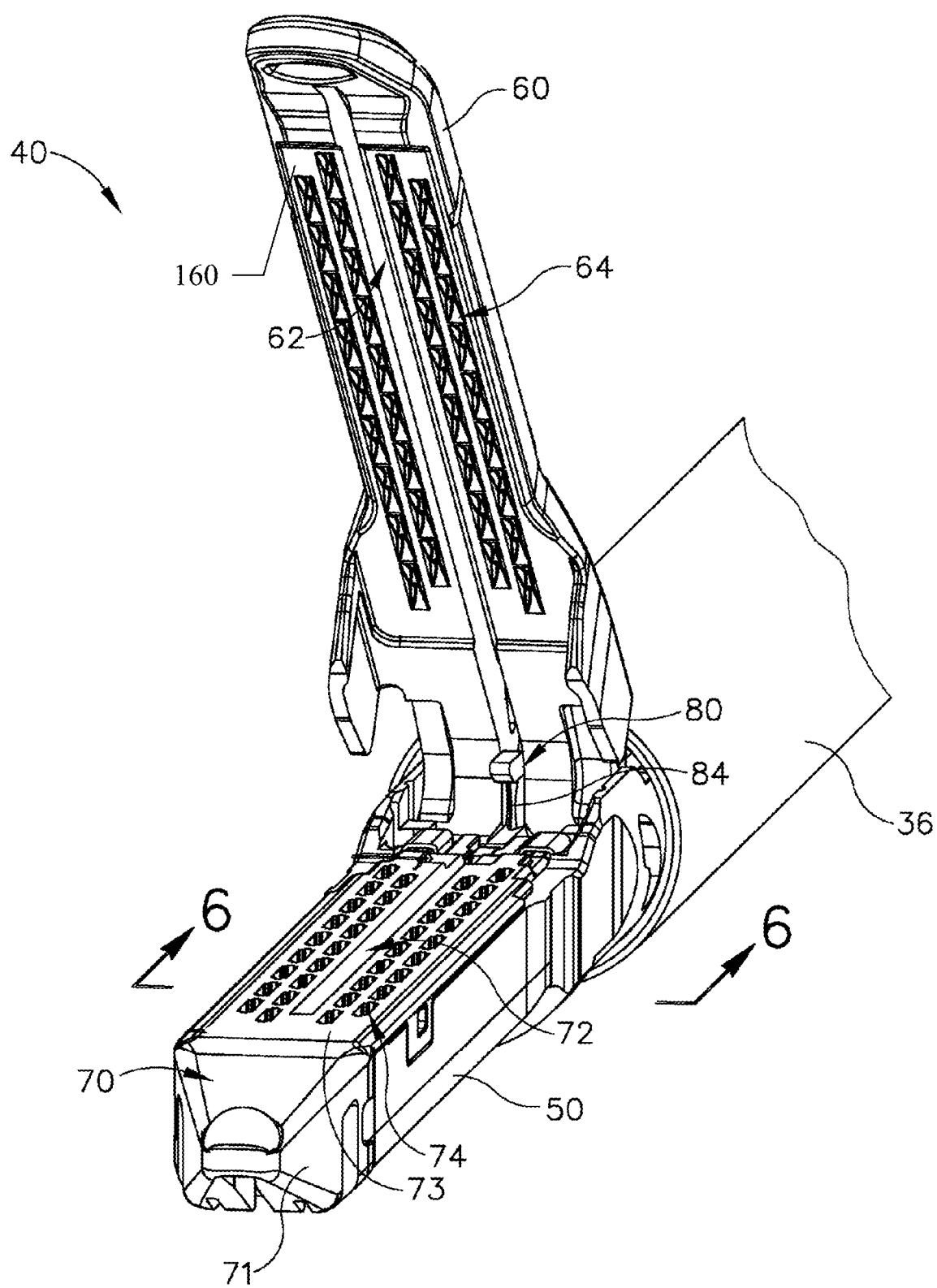
FIG. 4 depicts a perspective view of the end effector of FIG. 3, with the end effector in an open configuration.
Figure 5:
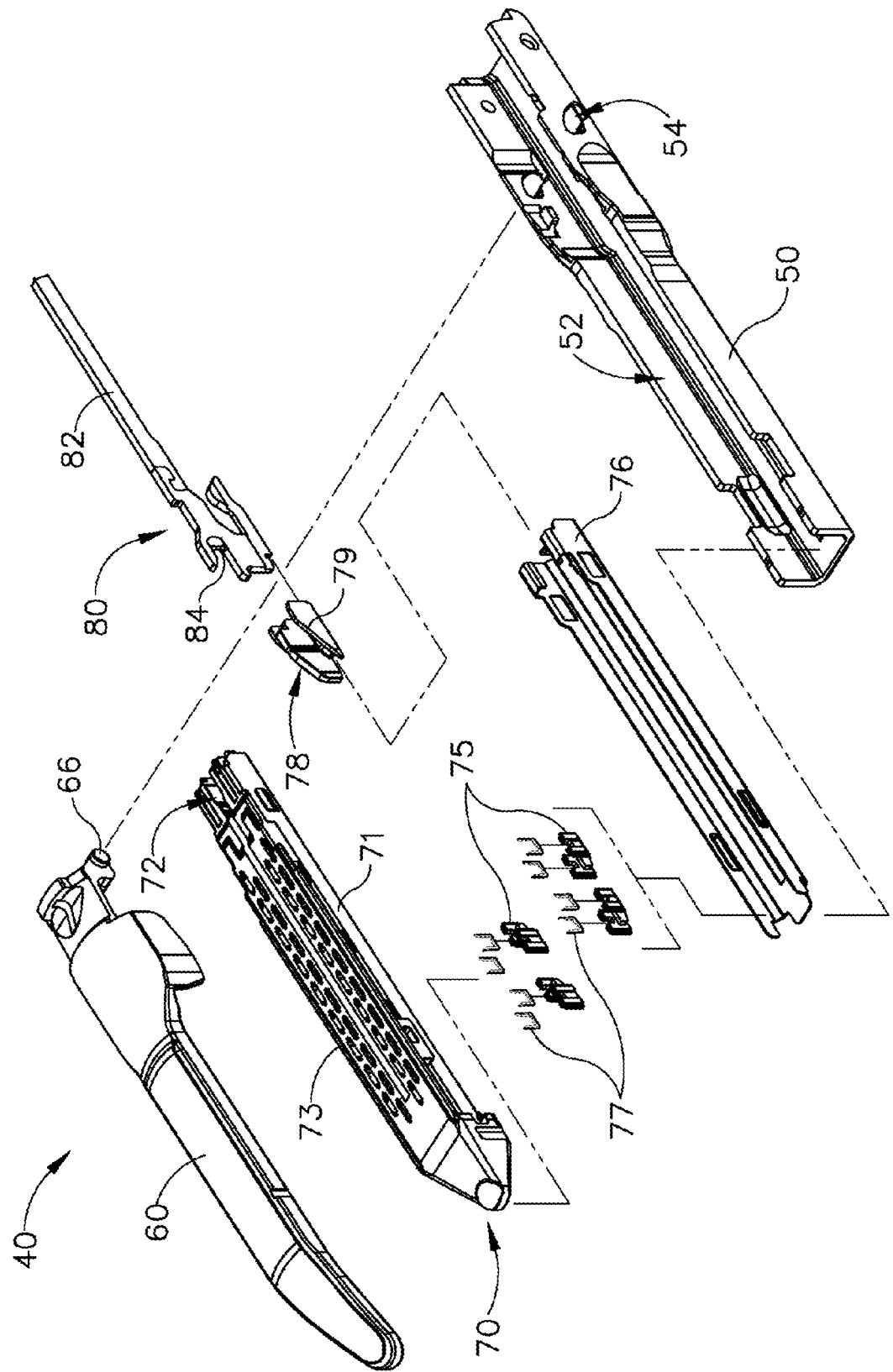
FIG. 5 depicts an exploded perspective view of the end effector of FIG. 3.

As seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). Staple forming pockets (64) are configured to bend the legs of staples (77) to secure the formed staples (77) in the tissue.

Figure 6:
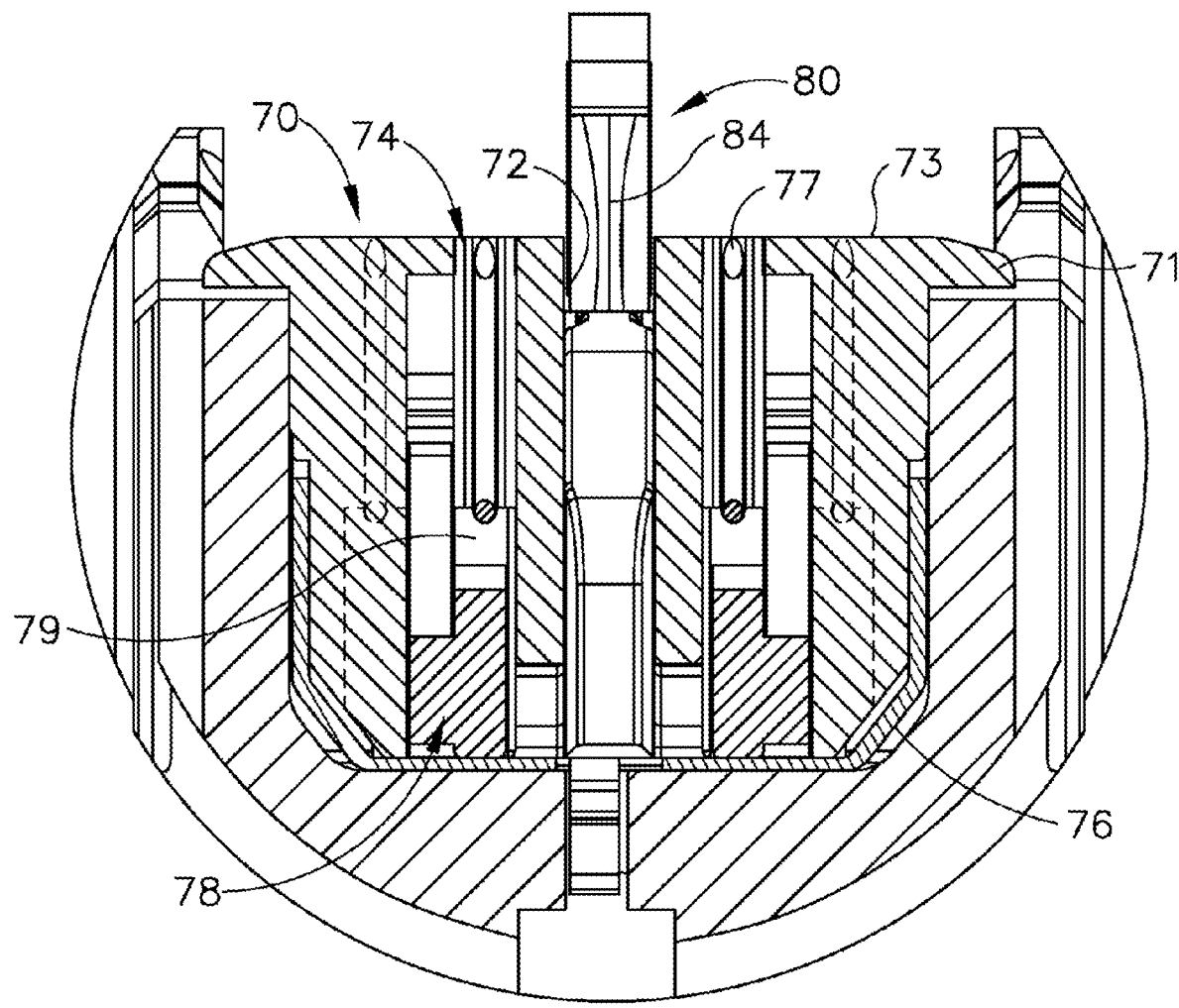
FIG. 6 depicts a cross-sectional end view of the end effector of FIG. 3, taken along line 6-6 of FIG. 4.
Figure 7:
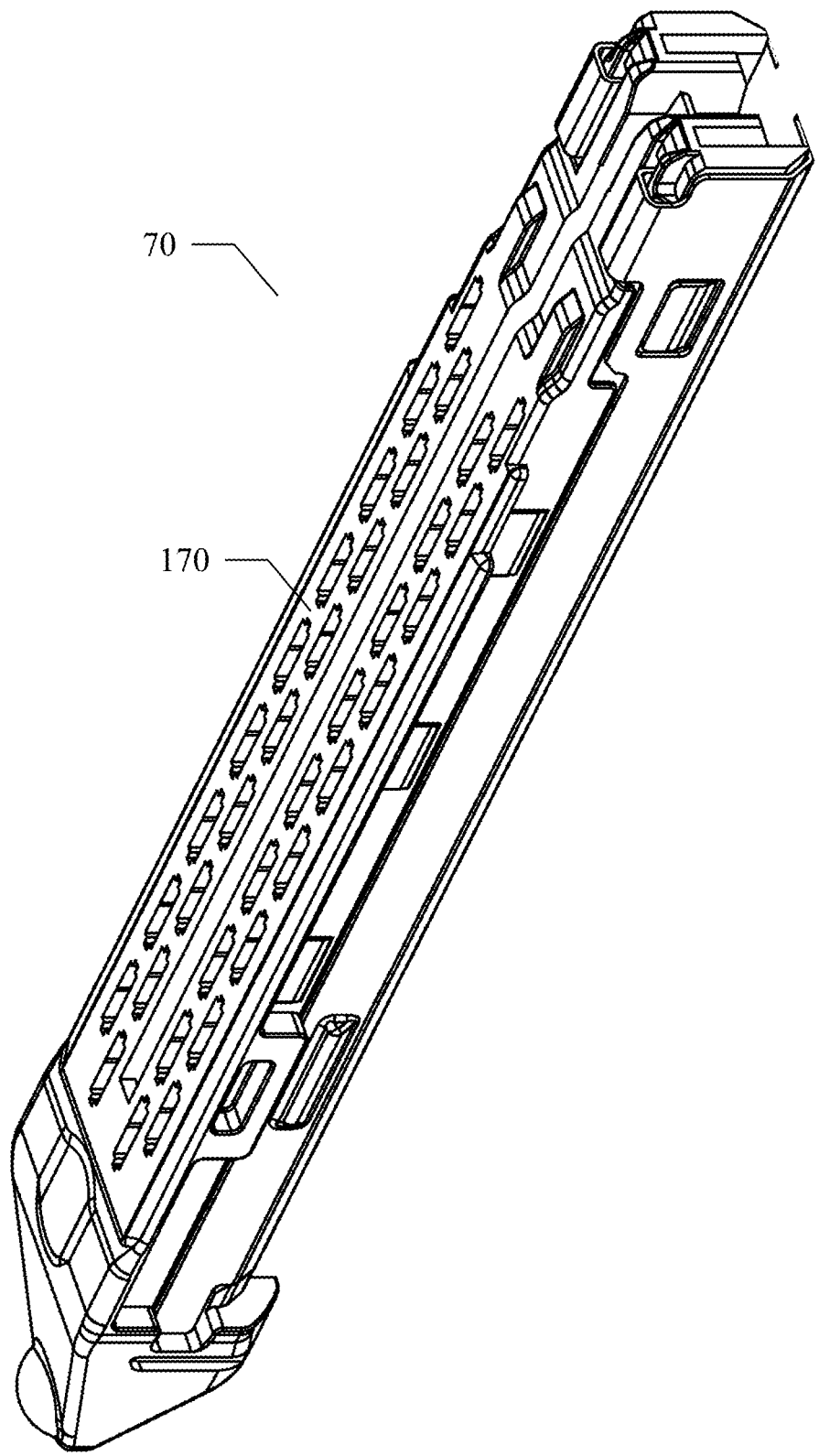
FIG. 7 depicts a perspective view of an exemplary cartridge that may be incorporated into the end effector of FIG. 3.

In the present example, a knife member (80) is configured to translate through end effector (40). As seen in FIG. 5, knife member (80) is secured to the distal end of a firing beam (82). As seen in FIGS. 4 and 6, knife member (80) is positioned in channels (62, 72) of anvil (60) and staple cartridge (70). Knife member (80) includes a distally presented cutting edge (84) that is configured to cut tissue that is compressed between anvil (60) and deck (73) of staple cartridge (70) as knife member (80) translates distally through end effector (40).

In some versions, end effector (40) includes lockout features that are configured to prevent knife member (80) from advancing distally through end effector (40) when a staple cartridge (70) is not inserted in lower jaw (50). In addition, or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). Alternatively, end effector (40) may simply omit such lockout features.

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40).

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features may be used to actuate anvil (60).

Figure 8:
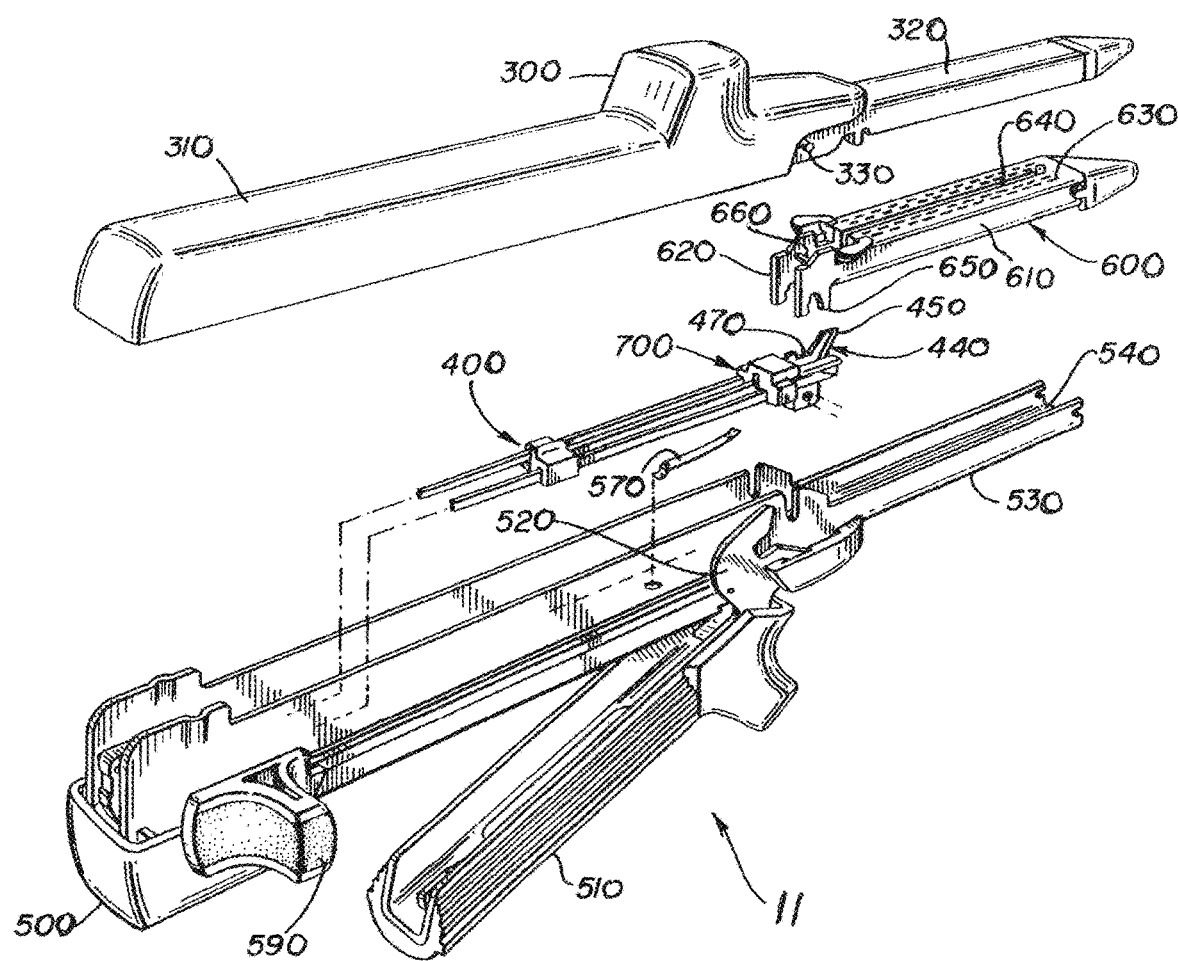
FIG. 8 shows an exploded perspective view of an alternative exemplary surgical stapling instrument.

Referring now to FIG. 8, an alternative exemplary surgical stapling instrument or linear stapler device is shown, with the figure adapted from the U.S. Pat. No. 5,275,323 "Surgical stapler" and incorporated by reference herein in its entirety. As seen in FIG. 8, surgical stapler 11 comprises an upper piece 300, a firing means 400, a lower piece 500 and a staple cartridge 600.

Staple cartridge 600 fits within the lower piece 500. Specifically, the front part of staple cartridge 600 fits into lower jaw channel 540. More specifically, the parallel side walls 610 of the staple cartridge 600 fit within the lower jaw channel 540. The back part of staple cartridge 600 has a breakable transverse member 660. This breakable transverse member 660 is placed on top of cartridge locking means 470 of firing means 400. At the same time two legs 650 within rearwardly extending surfaces 620 secure staple cartridge 600 to lower piece 500.

In FIG. 8, upper piece 300 has a rear upper handle portion 310 and a front upper jaw portion or anvil 320. Likewise, lower piece 500 includes a rear movable lower handle portion 510 and a front lower jaw portion 530. The embodiment of the surgical stapler as illustrated in FIG. 8 incorporates firing means 400, leaf spring 570, and staple cartridge 600 into lower piece 500. Yet, these elements may be placed in upper piece 300 instead of lower piece 500.

Lower handle portion 510 illustrated in FIG. 8 is movable, more specifically, pivotable between two locking positions. In the first locking position, movable lower handle portion 510 is positioned at an oblique angle to lower jaw portion 530. During the first locking position, a C-shaped member 520 of lower handle 510 is disengaged from a stationary locking pin 330. The upper and lower pieces, 300 and 500, respectively may be separated before or after operation of stapler 11 in the first locking position. On the other hand, in the second locking position the C-shaped member 520 of movable lower handle 510 locks the upper and lower pieces 300 and 500 together. In the second locking position, the movable lower handle portion 510 is parallel to lower jaw portion 520. This second locking position occurs by engaging stationary locking pin 330 with C-shaped member 520. This movable handle portion design may be on the upper or lower handle portions, 310 and 510, respectively.

Firing knob 590 activates firing means 400. Firing means 400 also includes a roof assembly 700 and contains a cutting means such as a knife blade assembly 440. A cutting surface 450 is included in knife blade assembly 440. Although a knife blade assembly is illustrated in FIG. 8, tissue may be cut in many ways besides knife or razor blade cutting.

When knife blade assembly 440 is in alignment with slot 640, firing knob 590 is manually pushed towards staple cartridge 600. Pushing firing knob 590 moves knife blade assembly 440 forward toward the staple cartridge 600. Then knife cutting surface 450 is moved through slot 640 of staple cartridge 600 simultaneously advancing staples from staple cartridge 600 through longitudinal slots 630. In some staple cartridge 600 embodiments, knife blade assembly is incorporated into the staple cartridge 600.

Other versions and modifications of the surgical staplers 10, 11 are known to a skilled artisan, all including a staple cartridge 70 or 600 having a plurality of staple pockets 74 or longitudinal slots 630 containing staples 77 (staples are not shown in FIG. 8), with staple pockets 74 or longitudinal slots 630 typically arranged in one or several rows on both sides of longitudinally extending channel 72 or slot 640. There are typically at least two and frequently at least three rows of staple pockets 74 or longitudinal slots 630 on each side of longitudinally extending channel 72 or slot 640, with staple pockets 74 or longitudinal slots 630 in each row typically staggered or offset relative to pockets or slots in the adjacent row, to improve the sealing and prevent leakage along the stapling line.

In the following description, descriptors and reference numerals associated with FIGS. 1-7 will be used for consistency, with the understanding that alternative structures such as these shown in FIG. 8 can also be used. Thus, when referring to staple cartridge, reference numeral 70 of FIGS. 1-7 will be utilized, with the understanding that the disclosure is also applicable to staple cartridge 600 of FIG. 8.

According to one aspect of the present invention, locally pre-cooling tissue immediately prior to stapling is beneficial for better surgical outcomes. Linear stapler has a cooled zone that enables cooling of tissue after the stapler is positioned on/in the tissue, immediately prior to stapling. Cooled zone is located in or on lower jaw (50 or 530) and/or anvil (60 or 320) in proximity to the tissue facing surfaces of anvil and/or lower jaw or and is represented by the below described coolant reservoirs containing pre-cooled coolants or instant coolant; coolant reservoirs connected to recirculating coolants; electrically cooled Peltier elements; compressed gas cooled throttling orifices connected to gas conduits and to sources of compressed gas; heat pipe transferring thermal energy between lower jaw and/or anvil and a cooling zone in stapler handle (20, 310, 510). Cooled zone is configured to transfer thermal cooling energy to the tissue facing surfaces so that tissues in contact with tissue facing surfaces are pre-cooled prior to stapling.

Figure 9:
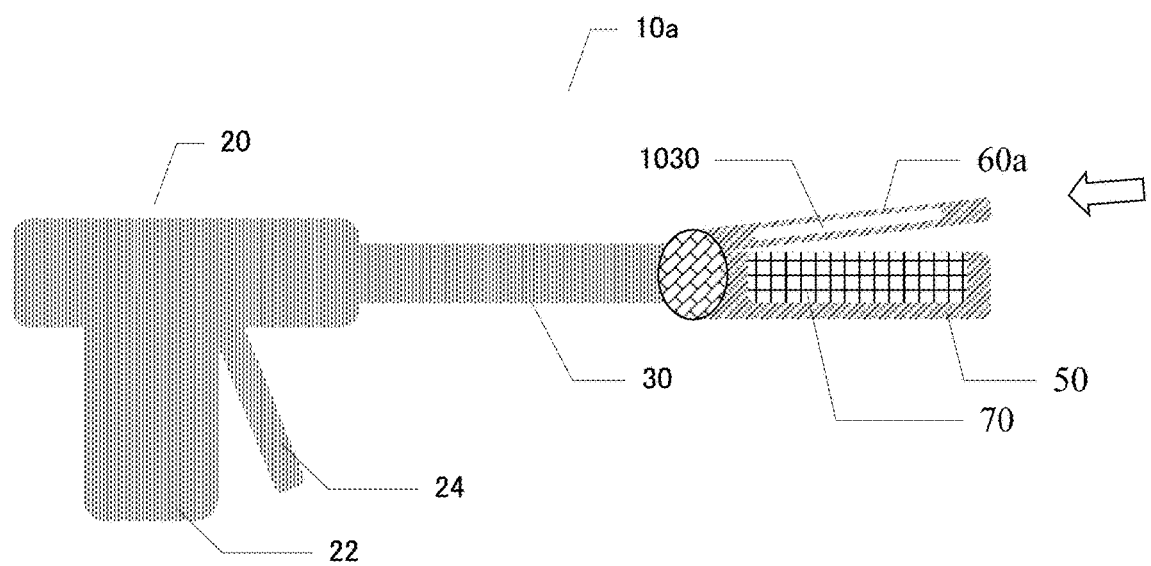
FIG. 9 shows a schematic cross-sectional view of assembled stapler of the present invention with a cooled zone in the anvil.

Turning now to FIG. 9, a simplified cross-sectional view of an embodiment of surgical stapling and cutting instrument 10*a* of the present invention is shown, with anvil 60*a* having a coolant chamber or coolant reservoir or coolant compartment 1030 inside.

Figure 10:
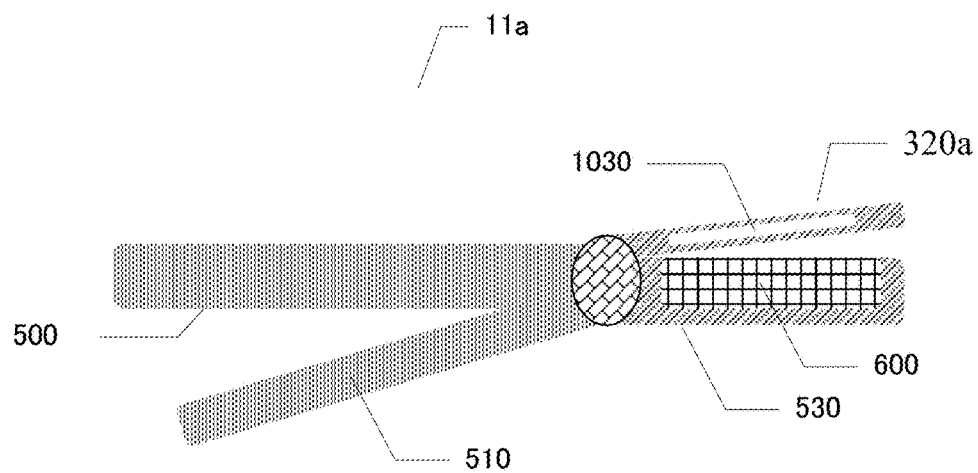
FIG. 10 shows a schematic cross-sectional view of an alternative assembled stapler of the present invention with a cooled zone in the anvil.

Similarly, FIG. 10 shows a simplified cross-sectional view of an embodiment of surgical stapler 11*a* of the present invention, with anvil 320*a* having a coolant chamber or coolant reservoir or coolant compartment 1030 inside.

Figure 11:
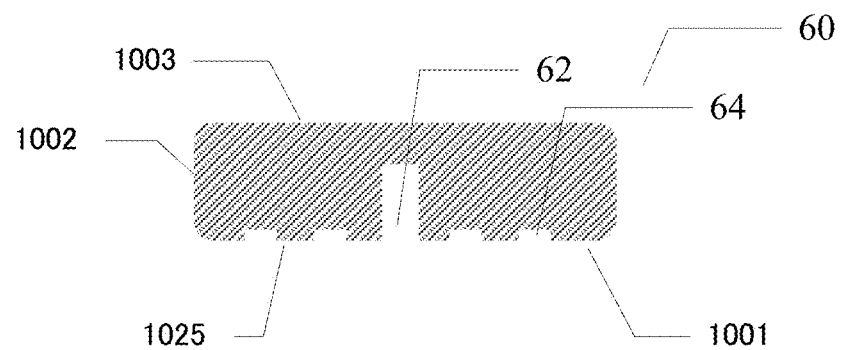
FIG. 11 shows a schematic cross-sectional view of a typical anvil.

FIG. 11 shows a simplified cross-sectional view of anvil 60 as known in the art, having no coolant compartment 1030, having upper portion 1003, sidewalls 1002, tissue facing end or staples facing surface 1001 with longitudinally extending channel 62 and a plurality of staple forming pockets 64 in the staple bending zone 1025. The cross-section is taken across the longitudinal axis of anvil 60 and view is from distal end of anvil 60.

Turning now to FIGS. 12A-12G, schematic cross-sectional views of anvil 60*a* of present invention are shown. The cross-section is taken across the longitudinal axis of anvil 60*a* and the view is from distal end of anvil 60 as shown by arrow in FIG. 9.

Figure 12A:
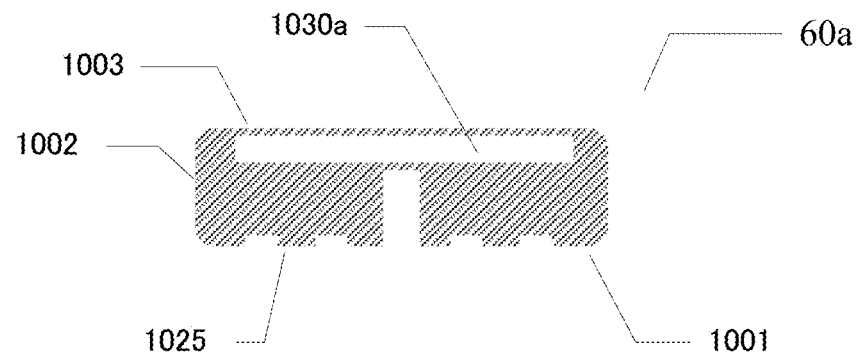
FIGS. 12A-12G show schematic cross-sectional views of anvils of the present invention.

FIG. 12A shows an embodiment of anvil 60*a* having an enclosed coolant chamber or coolant reservoir or coolant compartment 1030*a* inside, filled with a coolant. Coolant compartment 1030*a* can be of any shape, including rectangular, cylindrical, spherical, ellipsoidal, toroidal, cuboidal, pyramidal, cone-shaped, truncated cone or frusto-conical shaped, combinations of the above, etc. As shown, coolant compartment 1030*a* is generally rectangular and runs under upper portion 1003 between side walls 1002 across the width of anvil 60*a* and along the length of anvil 60*a*.

Figure 12B:
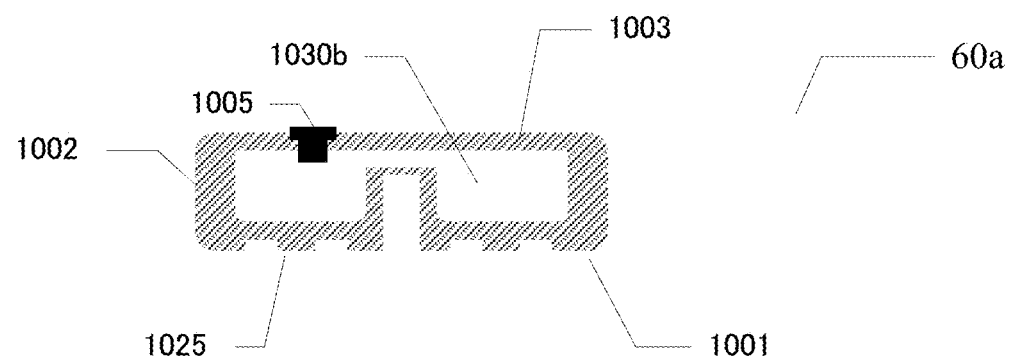

FIG. 12B shows an embodiment like one shown in FIG. 12A, but having expanded coolant compartment 1030*b* having larger subchambers close to side walls 1002 which is configured to take as much as possible of the available space inside anvil 60*a*. An optional fill port is shown terminating on upper portion 1003 and capped with a cap 1005. Coolant compartment 1030*b* is positioned in closer proximity to staple bending zone 1025 and staples facing surface 1001.

Figure 12C:
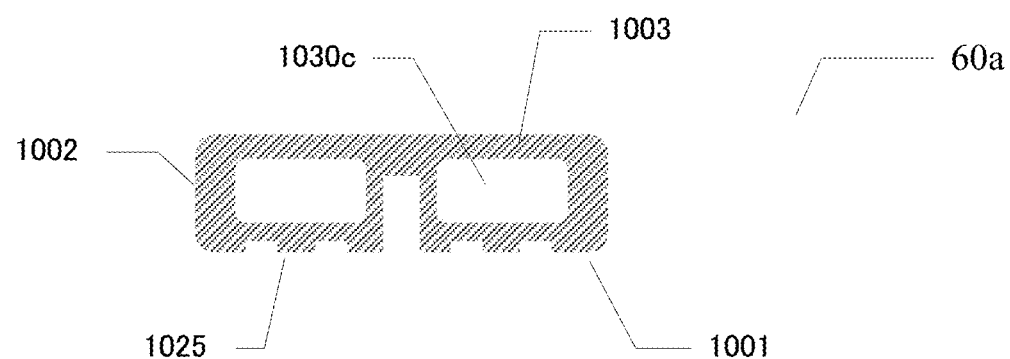

FIG. 12C shows an embodiment like one shown in FIGS. 12A, 12B, but having two unconnected subchambers of coolant compartment 1030*c* inside anvil 60*a*.

Figure 12D:
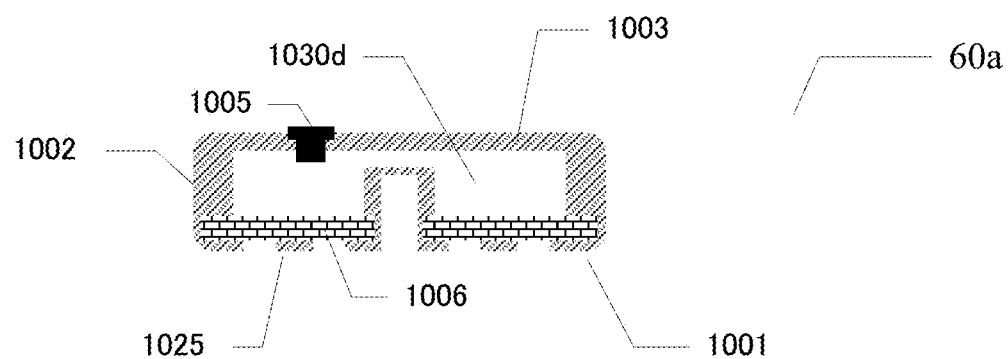

FIG. 12D shows an embodiment with an optional thermally conductive zone 1006 which extends from being in contact with coolant compartment 1030*d* towards staple bending zone 1025 and/over staples facing surface 1001. Optional thermally conductive zone 1006 is forming staple bending zone 1025 and/over staples facing surface 1001 and is made of any highly thermally conductive metal or alloy, including but not limited to copper or copper based alloy, aluminum or aluminum alloy, brass, and similar, with highly thermally conductive metal or alloy having thermal conductivity in excess of thermal conductivity of stainless steel, such as at least double the thermal conductivity of stainless steel, more preferably five times higher than thermal conductivity of stainless steel. This configuration is facilitating heat transfer and cooling of tissues adjacent to and in contact with staple bending zone 1025 and/or staples facing surface 1001 and prevents heat transfer and cooling of tissues not adjacent and not in contact with staple bending zone 1025 and/or staples facing surface 1001.

Figure 12E:
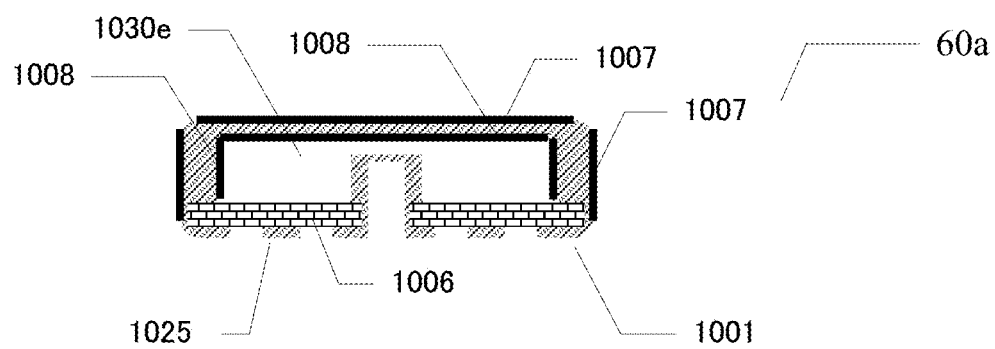

FIG. 12E shows an embodiment further having an optional thermally insulating external coating 1007 on external surfaces of anvil 60*a*, such as on sidewall 1002 and/or upper portion 1003 but not covering staple bending zone 1025 and/or staples facing surface 1001, regardless of whether optional thermally conductive zone 1006 is present (as shown) or not. Also shown is optional thermally insulating internal coating 1008 on internal surfaces of coolant compartment 1030*e*, not covering portions of coolant compartment 1030*e* adjacent to staple bending zone 1025 and/or staples facing surface 1001, regardless of whether optional thermally conductive zone 1006 is present (as shown) or not. This configuration is facilitating heat transfer and cooling of tissues adjacent to and in contact with staple bending zone 1025 and/over staples facing surface 1001 and prevents heat transfer and cooling of tissues not adjacent and not in contact with staple bending zone 1025 and/or staples facing surface 1001.

In all embodiments, thermal energy of coolant contained in compartments 1030 is used to facilitate heat transfer from tissue to coolant and to cool tissue immediately prior to stapling.

Figure 12F:
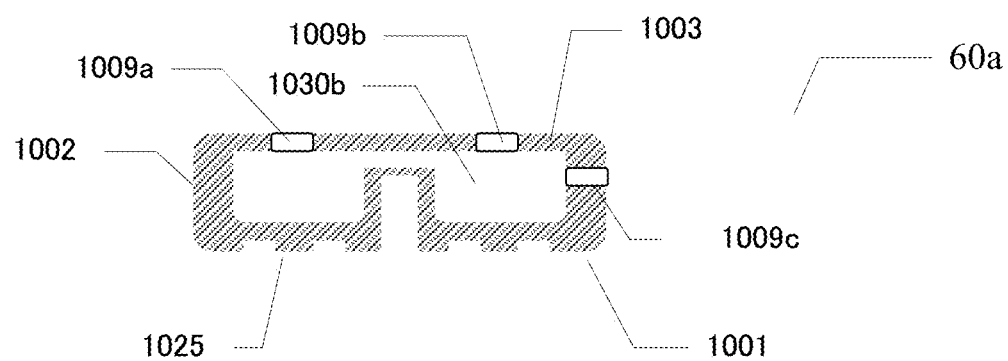

Referring to FIG. 12F, at least one or more optional windows 1009*a*, 1009*b*, 1009*c* are installed on upper portion 1003 and/or sidewall 1002, the windows can then be utilized to detect two-phase ice/water mixture presence in coolant compartments 1030*b* indicating temperature of 0° C. in case of pure water and another temperature in case of cooling mixtures, such as salt/water cooling mixtures with lower temperature of liquid/frozen equilibrium.

Figure 12G:
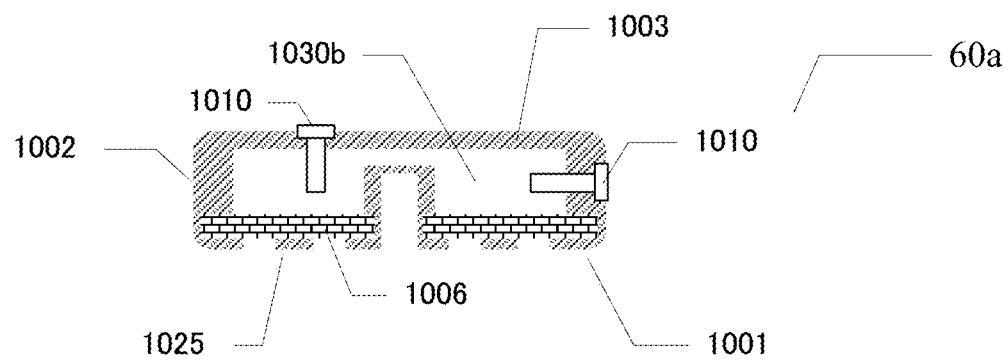

Referring to FIG. 12G, an optional temperature probe, sensor, or indicator 1010 can be installed on anvil 60*a*, such as on upper portion 1003 or side wall 1002, including electronic indicator, color change indicator, bi-metallic temperature indicator, etc. Temperature probe 1010 can also comprise a port for measuring electric output from a thermocouple, thermistor, and similar sensor installed inside compartments 1030*b*.

According to at least some embodiments of the present invention, coolant reservoirs or compartments 1030 contain coolant, preferably a fluid coolant, that preferably has high heat capacity or thermal capacity and thus can store substantial amounts of cooling energy which is then transferred to tissue for tissue cooling immediately prior to stapling. High heat capacity or thermal capacity materials are characterized by high specific heat capacity, with preferred coolant being water, normal saline, or any aqueous solution. Pure water or water containing minor amounts of dissolved compounds can be used as a coolant, water having very high heat capacitance of about 4 J/g/K. Salt-water mixtures can be utilized for temperatures lower than 0° C.

Compartments 1030 can contain from 1 to 20 g of water, such as 1, 2, 3, 4, 5, 6, 7 g. Providing for instance 5 g of water inside compartments 1030 would result in the following cooling energy production. With water inside compartments 1030 initially at +5° C. heating to +10° C. during tissue cooling, cooling zone would absorb amount of energy from the surrounding area, which includes tissue, equal to about 5 g*5° C.*4=100 J.

Water is also characterized by very high enthalpy of fusion (latent heat of fusion), which is the amount of energy consumed or released during phase transition such as melting, with water having specific heat of fusion of about 334 J/g. In one embodiment, water inside coolant reservoirs or compartments 1030 is initially frozen i.e. converted into ice. The amount of energy absorbed from the surrounding area as the ice is melting at 0° C., will be equal to about 5 g*334=1670 J. If the melted water is then heated to +10° C., the additional amount of energy consumed and absorbed from the surrounding area, which includes tissue, is equal to about 5 g*10° C.*4=200 J. Considering that the weight of target tissue is comparable to from 1 to 5 g, it is expected that the target tissue can be substantially cooled below normal tissue temperature of 36.6° C., such as cooled to +3 . . . +15°

C., such as cooled to temperature of about +5, +7, +10° C. during brief contact with anvil 60*a* immediately prior to stapling, such as within 5-300 seconds, more preferably 10-120 s, such as 10, 20, 30, 60 s.

It is preferred that there is no freezing of tissue on contact with hypothermic or cooled anvils 60*a* of the present invention, and no permanent tissue damage. Accordingly, the temperature of the surfaces in contact with tissue is configured to be below tissue temperature, such as from about −10° C. to about +10° C. or even up to 20° C., such as −5, −3, 0, +3, +5° C., +10° C. For purposes of this disclosure, the term "hypothermic" means to effectively lower the temperature of tissue relative to normal body temperature in the immediate vicinity of the device by some artificial means as described further herein.

In some embodiments, coolant fluid comprises a material or a mixture having freezing point higher or lower than 0° C. In one embodiment, water-salt mixtures, water alcohol mixtures, and water-glycerol mixtures are used, all having freezing point lower than 0° C. In one embodiment, a mixture of water with glycerol is used that has the freezing point above 0° C., with concentration glycerol (% weight) of between 90% and 98.3% resulting in freezing points between −1.7° C. and +13° C., particularly concentrations from 93% to 95% of glycerol are useful for creating melting or freezing points of mixtures above 0° C. but below +8° C.

Cooling of tissue is intended not to result in any permanent damage of tissue or freezing of tissue. While cooled compartments can be below 0° C., when tissue itself is cooled below 0° C., it is performed only transiently and for brief periods of time, such as 1 s, 3 s, 10 s, 20 s. Similarly, when tissue is cooled to low temperature such as 5° C., it is performed also only transiently and for brief periods of time, such as 3 s, 10 s, 20 s, 60 s.

Figure 13A:
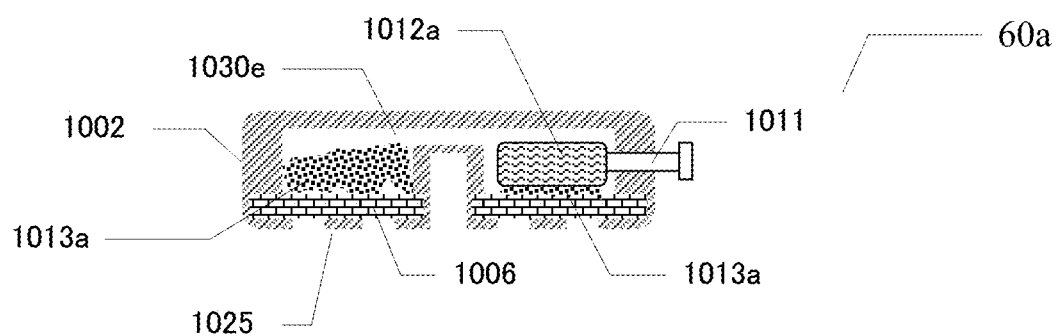
FIGS. 13A-13B show schematic cross-sectional views of anvils of the present invention.

In some embodiments, instant cooling is provided inside compartments 1030 using endothermic reactions of dissolving salt in water. The salts used can be ammonium nitrate, calcium ammonium nitrate, urea, or similar, whereby the salts are separated from water by a frangible separator or membrane. Referring to FIG. 13A, in one embodiment, salts 1013*a* having high endothermic enthalpy of dissolution are filled into compartment 1030*e*, with frangible bag 1012*a* containing water also placed inside compartment 1030*e*. An actuating lever 1011 configured to be accessible from outside of anvil 60*a* and adapted to reach frangible bag 1012*a* inside compartment 1030*e* is provided. Actuation of lever 1011 to break frangible bag 1012*a* releases water from bag 1012*a* resulting in mixing of salts with water dissolving the salts in an endothermic reaction and instant cooling of anvil 60*a*.

Figure 13B:
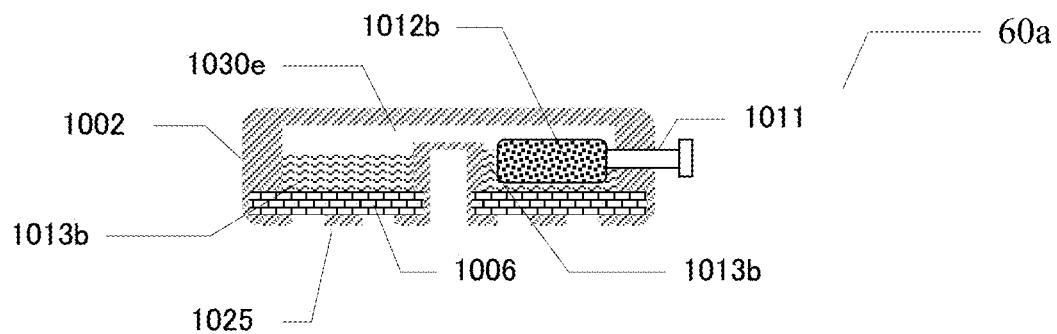

Referring to FIG. 13B, in another embodiment, salts are enclosed in a frangible bag 1012*b* placed inside compartment 1030*e* filled with water 1013*b*. Actuation of lever 1011 to break frangible bag 1012*b* releases salts from bag 1012*b* resulting in mixing of salts with water dissolving the salts in an endothermic reaction and instant cooling of anvil 60*a*.

Instant coolant mixture can be activated for producing cooling prior to any contact with tissues being joined, or after compressing tissues immediately prior to stapling.

Figure 14A:
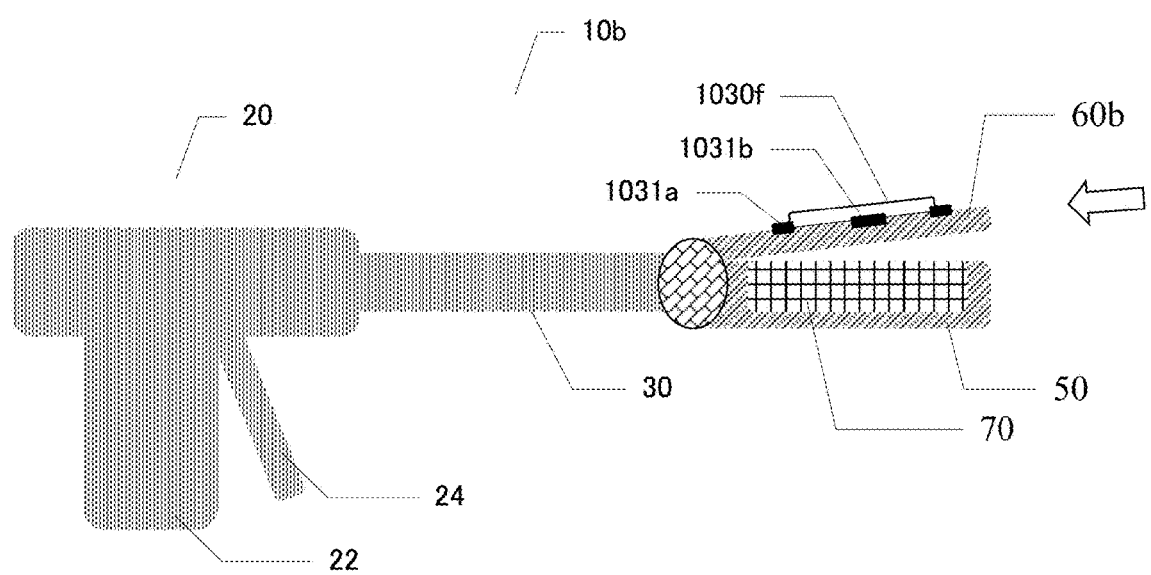
FIG. 14A shows a schematic cross-sectional view of assembled stapler of the present invention with attachable and detachable external coolant compartment on the anvil.
Figure 14B:
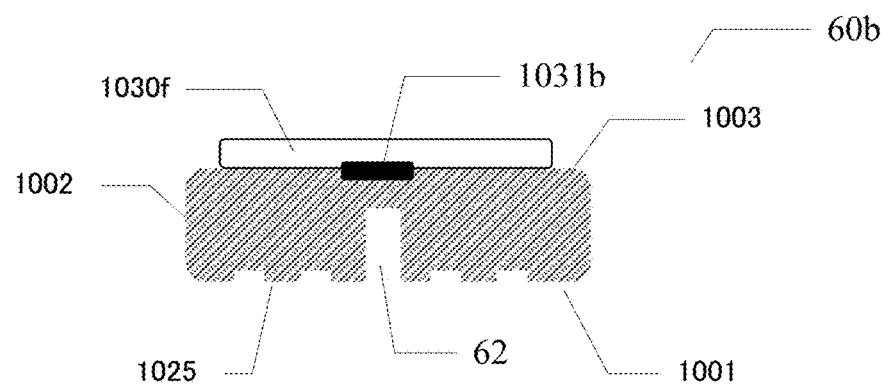
FIG. 14B shows a schematic cross-sectional view of anvil of the present invention.
Figure 14C:
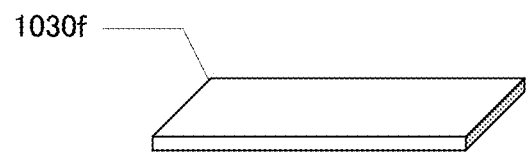
FIG. 14C shows a schematic perspective view of attachable and detachable external coolant compartment.

Referring to FIG. 14A, a simplified cross-sectional view of an embodiment of surgical stapling and cutting instrument 10*b* a of the present invention is shown, with anvil 60*b* having a coolant chamber or coolant reservoir or coolant compartment 1030*f* which is externally attached to anvil 60*b*. Referring further also to FIG. 14B, a simplified cross-sectional view of an embodiment of anvil 60*b* a of the present invention is shown with coolant compartment 1030*f* fixated on upper portion 1003 of anvil 60*b* via attachment fasteners 1031*b* located in the center of upper portion 1003 and/or fasteners 1031*a* located on the periphery of upper portion 1003. In all cases fasteners 1031*a*, 1031*b* enable snap-on rapid attachment and removal of coolant compartment 1030*f*. Attachable and detachable external coolant compartment 1030*f* comprises a generally rectangular elongated body as shown in FIG. 14C. In a preferred embodiment, external coolant compartment 1030*f* is hollow and is filled with coolant. In an alternative embodiment, external coolant compartment 1030*f* comprises solid non-hollow body that is made of metal.

Similarly, relative to the inventive embodiments shown above, with cooled zone located in or on anvil 60*a*, 60*b*, 320*a*, cooled zone comprising coolant reservoirs or coolant compartments can be also positioned in or on the lower jaw (50 or 530) (not shown).

In some embodiments (not shown), there is provided an optional thermally conductive zone like thermally conductive zone 1006 which extends from coolant compartment to staple-deploying tissue facing surfaces of stapling cartridge 70, 600.

In some embodiments (not shown), instant cooling is provided inside cooling compartments using endothermic reactions of dissolving salt in water, like embodiments of FIGS. 13A, 13B, with an actuating lever like actuating lever 1011 configured to be accessible and adapted to reach frangible bag inside cooled compartment.

Figure 15:
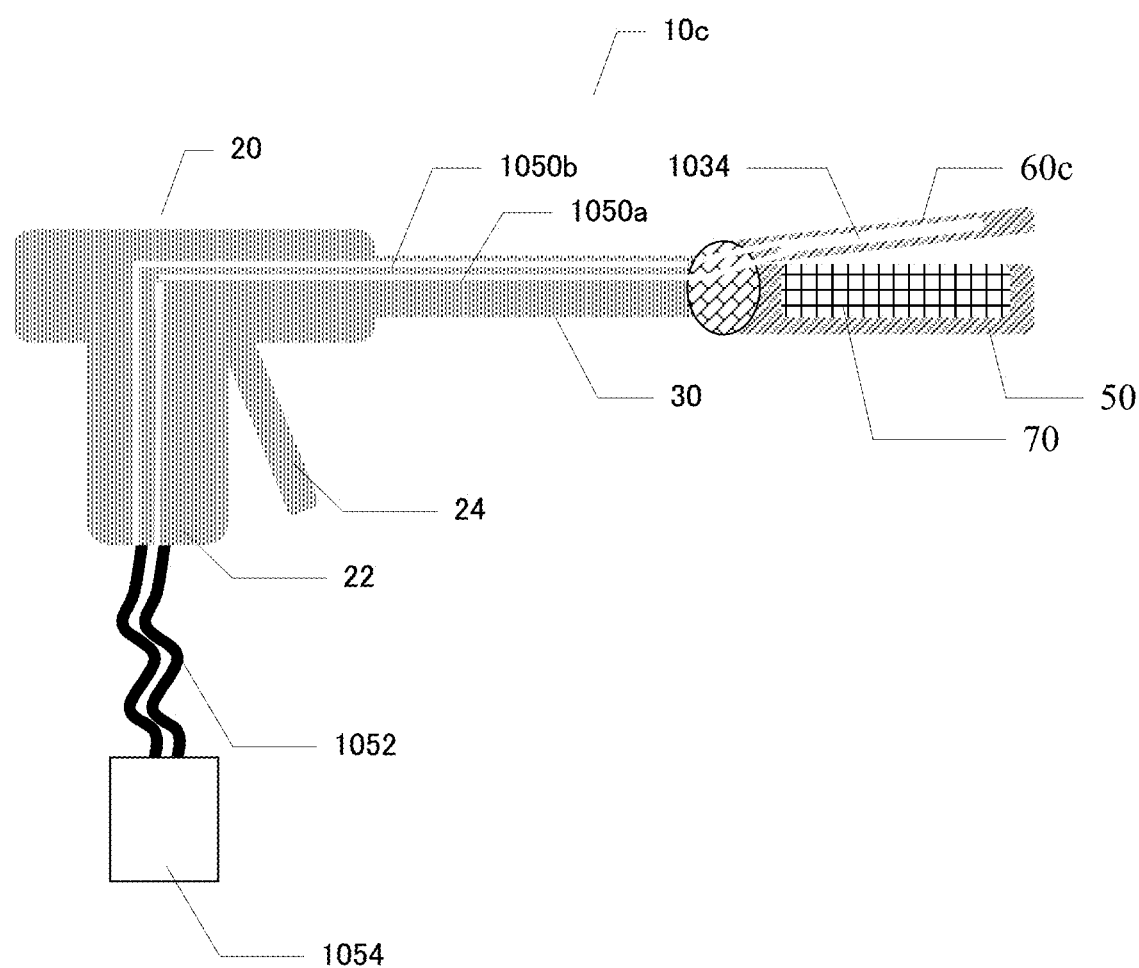
FIG. 15 shows a schematic cross-sectional view of assembled stapler of the present invention.

Referring now to FIG. 15, in some embodiments of surgical stapling and cutting instrument 10*c* of the present invention, there is provided in anvil 60*c* a recirculation coolant reservoir or cooling compartment 1034, into which chilled coolant is supplied via supply channel 1050*a* and drain channel 1050*b*, such channels terminating close to or on handle assembly 20, such as on pistol grip 22 as shown, and connected to supply/drain lines 1052 which are connected to a pump and chiller 1054 adapted to supply cooled fluid coolant. Pump and chiller 1054 can be positioned outside of stapler 10*c* (as shown) or inside (not shown). In operation, recirculation of cooled fluid coolant lowers the temperature of anvil 60*c* to a desired temperature from about 0° C. to about 10° C. such as 5° C. Recirculation can continue during stapling operation or can be stopped prior to stapling. Coolant reservoir or cooling compartment 1034 can comprise a chamber or a tubular coil.

Optionally, prior to stapling, anvil 60*c* is brought into contact with lower jaw 50 and pre-cooled using conductive heat transfer for several minutes, such as 5-60 minutes.

Figure 16:
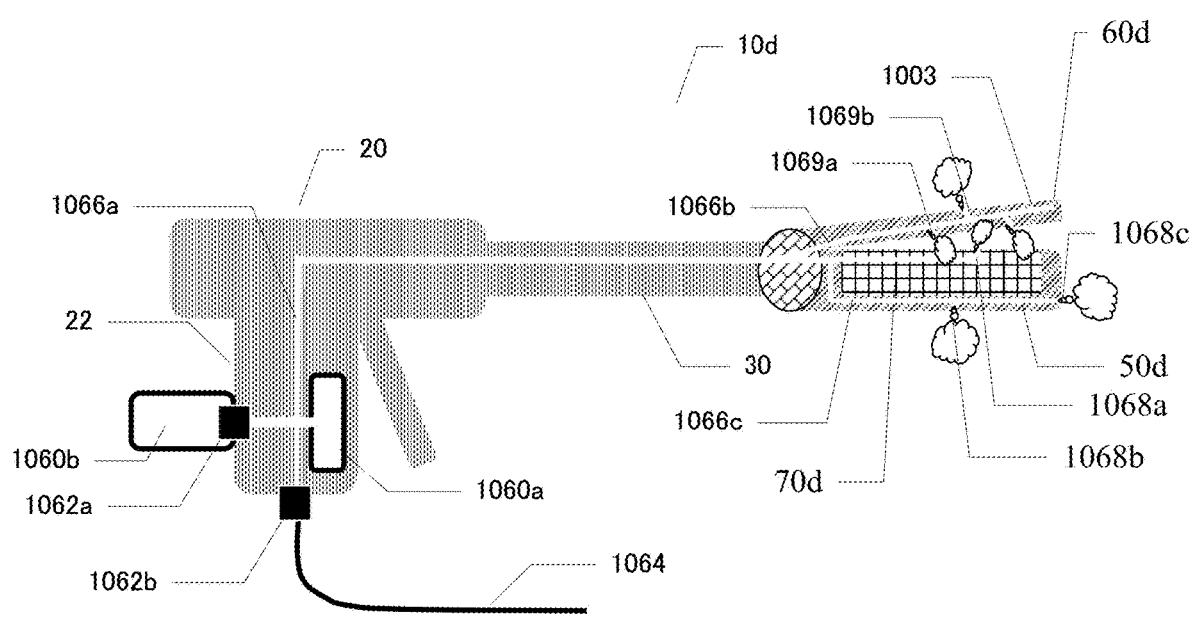
FIG. 16 shows a schematic cross-sectional view of assembled stapler of the present invention.

According to another embodiment of surgical stapling and cutting instrument 10*d* of the present invention schematically shown in a cross-sectional view in FIG. 16, cooling and/or pre-cooling of anvil 60*d* and or lower jaw 50*d* and/or stapling cartridge 70*d* is performed by a throttling process or Joule-Thomson process or adiabatic expansion cooling, whereby compressed gas is allowed to expand and exit into the surrounding space through a throttling orifice, valve, or porous permeable plug from a higher to a lower pressure. Referring to FIG. 16, source of compressed gas, such as air, $CO_2$, nitrogen, or similar, is provided. Source can be a balloon with compressed gas, such as balloon 1060*a* located inside pistol grip 22, balloon 1060*b* located proximal to handle 20 and connected to it via gas port 1062*a*, or source of compressed gas can be (not shown) distal to handle 20 and connected to a gas port 1062*b* via gas supply line 1064.

A gas conduit line 1066*a* is configured to carry compressed gas from handle 20 area towards anvil 60*d* and/or lower jaw 50*d*, terminating at one or more throttling orifices, located as shown, with conduit line 1066c in lower jaw 50d feeding throttling orifices 1068a located anywhere on stapling cartridge 70d, throttling orifices 1068b and 1068c located on lower jaw 50d.

A gas conduit line 1066b is configured, additionally or alternatively, to carry compressed gas supplied by conduit 1066a from handle 20 area towards anvil 60d, terminating at one or more throttling orifices, located as shown, with throttling orifices 1069a located on tissue facing surface of anvil 60d, and throttling orifices 1069b located on upper portion 1003 of anvil 60d.

Compressed gas released from throttling orifices 1068, 1069 is schematically shown in FIG. 16 by a gas cloud symbol. The diameters of throttling orifices 1068, 1069 are from about 20 to about 2000 microns, such as 30, 50, 100, 200, 300, 500, 800, 1000, 1500 microns.

Cooling by compressed gas can be performed prior to compressing tissue between anvil 60d and lower jaw 50d, utilizing any or all of throttling orifices 1068, 1069. Cooling by compressed gas can be also performed after compressing tissue between anvil 60d and lower jaw 50d, but prior to stapling, by utilizing only throttling orifices that are not positioned on tissue facing surfaces, i.e. utilizing throttling orifices 1069b and/or 1068b, 1068c.

In an alternative embodiment, there is provided a cooled zone comprising a Peltier element (not shown) positioned with its cold plate proximal to tissue facing surfaces of cartridge 70, 600, or more preferably to tissue facing or staples facing surface 1001 of anvil 60a. Supplying electric energy to the Peltier element results in cooling of the tissue facing surfaces.

In a still further embodiment, the cooled zone can include a heat pipe configured to transfer thermal energy between lower jaw and/or anvil and a heat sink zone in the stapler handle.

In operation of all embodiments, the cooled surfaces which are in contact with tissues are maintained close to or at above tissue freezing temperature, such as above −3, −2, −1, 0° C., most preferably above 0° C., such as at 0, +1, +2, +4, +5, +6, +8, +10° C., to avoid freezing of tissue to the stapler and to avoid thermal injury to tissue. In some embodiments, cooled zone is at temperature below tissue freezing temperature, such as at −10° C., but upon contact with tissue and heat exchange between cooled zone and tissue, temperature rapidly raises to above tissue freezing such as above 0° C., such as reaching 0, 3, 5° C.

Figure 17:
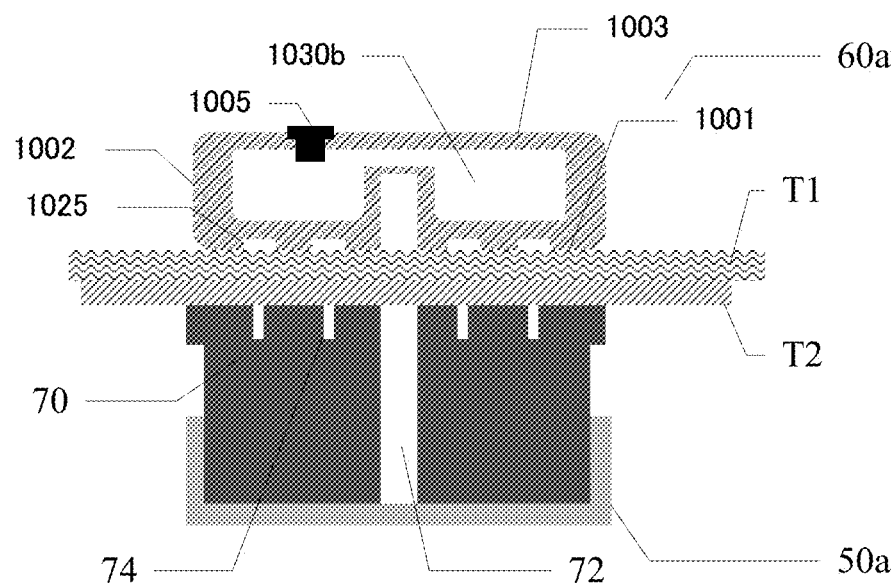
FIGS. 17 and 18 show schematic cross-sectional view of components of stapler of the present invention in operation.

Referring now to FIG. 17, a schematic cross-sectional view of anvil 60a and lower jaw 50a with stapling cartridge 70 is shown with anvil 60a approximated to cartridge 70 in preparation to stapling and resecting upper tissue T1 and lower tissue T2 which tissues are compressed between anvil 60a and cartridge 70 (lower jaw 50a). Upper tissue T1 is in contact with anvil 60a staple bending zone 1025 and staples facing surface 1001 while lower tissue T2 is in contact with stapling cartridge 70 and lower jaw 50a.

The position shown is prior to deployment of staples. For simplification, the mechanism of staples deployment from staple pockets 74 and mechanism of deploying tissue cutting knife through channel 72 are not shown. For simplification, anvil 60a is shown as embodiment like the embodiment of FIG. 12B having coolant compartment 1030b. However, any of the above embodiments of anvil 60 and cooling elements of anvil 60 can be utilized, including coolant compartments 1030 in or on anvil, containing coolant and/or frozen coolant; instant coolant utilizing endothermic reactions of dissolving salt in water; recirculating coolant; electric cooling embodiments; compressed air cooling embodiments. Similarly, any of the above embodiments of lower jaw 50 can be utilized.

All the above elements facilitating cooling of anvil and/or lower jaw can be activated prior to compressing tissues T1 and T2 between anvil 60a and cartridge 70 (lower jaw 50a). Additionally, instant coolant, recirculating coolant; electric (Peltier) cooling elements can be activated before or after compressing tissues T1 and T2. Additionally, the gas cooling mechanism throttling orifices not facing tissues T1 and T2 can also be activated before or after compressing tissues T1 and T2 as explained above.

As can be appreciated from FIG. 17, once tissues T1 and T2 are compressed between anvil 60a and cartridge 70 (lower jaw 50a), tissues T1 and T2 are being cooled by conductive heat transfer, specifically in the areas of contact with anvil 60a and/or cartridge 70. Such cooling can be performed for any convenient period as preparations for stapling are made, preferably for at least 5-10 seconds, such as 10, 20, 30, 60, 120, 300, 600 s.

After compressed tissues T1, T2 are substantially cooled, for instance brought to temperatures below body temperature of 36.6° C., such as to temperatures from about 3° C. to about 20° C., such as 5, 10, 15, 20° C., stapling is actuated, staples (not shown) deploy from stapling cartridge 70 and join tissues T1 and T2 while simultaneously optionally resecting tissues between stapling lines.

Figure 18:
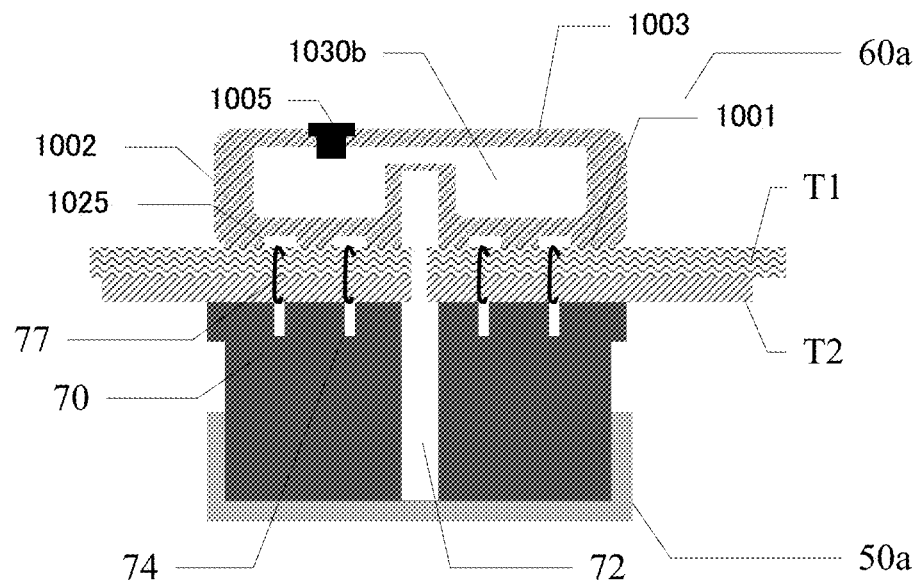

Referring now to FIG. 18, the configuration of embodiment of FIG. 17 is shown after stapling, i.e. after staples 77 deployed thus establishing a stapled joint between tissues T1 and T2 and with tissues cut by knife member.

After deploying staples 77 and cutting tissues, linear stapler is withdrawn by opening or separating anvil 60a and lower jaw 50a. Advantageously, areas of cut and stapled tissues T1 and T2 are beneficially protected from excessive injury by pre-cooling these areas. Linear stapler can be withdrawn immediately after stapling. In an alternative embodiment, cooling of just stapled and resected tissues is continued for a brief period by continuing compressing stapled tissues for at least additional 5 s, such as for 10, 30, 60, 300, 600 s.

According to embodiments of the present invention, the sequence of using or operating linear staplers 10a, 11a, 10b, 10c, 10d while joining tissues is as follows:
  a) Positioning tissues T1 and T2 between anvil 60a and lower jaw 50a;
  b) Approximating anvil 60a and lower jaw 50a and compressing tissues T1 and T2 between anvil 60a and lower jaw 50a;
  c) Firing stapler 10a and establishing stapled joint between tissues T1 and T2; and
  d) Opening or separating anvil 60a and lower jaw 50a and withdrawing stapler 10a from contact with tissues T1 and T2.

Complete and all steps for stapling and resecting surgical procedures are not listed above, but will be known to skilled artisans. The temperature of cooling zone can be in the ranges of −10 C. to +20 C. or shift from +20 C. to −10 C. over a short period of time and does not have to stay constant during contact with tissue. The temperature of tissue can decrease upon contact with hypothermic stapler and/or cooling zone from normal tissue temperature to at least 5 degrees Celsius lower, such as 5, 10, 15, 20, 30, 40° C. lower. In some embodiments, tissue temperature in the areas to be stapled is decreased to reach 0, 5, 10° C.

According to the embodiments of the present invention, cooling related steps are performed as per the following sequences:

Coolant in coolant compartments and externally attached cooling chamber embodiments. Coolant in coolant compartments 1030 is pre-cooled or frozen prior to positioning tissues T1 and T2 between anvil 60a and lower jaw 50a as outlined in step a) above. Similarly, externally attached cooling chamber 1030f is pre-cooled or frozen prior to positioning tissues T1 and T2 between anvil 60a and lower jaw 50a as outlined in step a) above.

Instant Coolant embodiments. Instant cooling mixture in compartments 1030e is activated prior to step a) or prior to step c) as outlined above. Most preferably instant cooling mixture is activated prior to step a).

Recirculation cooling embodiments. Cooling in recirculation cooling compartment 1034, is initiated or activated prior to step a), or prior to step b) or prior to step c). Cooling is effected by recirculation of coolant and it can be stopped after cooled compartment is sufficiently cooled, optionally stopping recirculation prior to steps a), b), or prior to step c), or prior to step d) as outlined above. Alternatively, recirculation of coolant continues from before step a) to after step d).

Electric cooling can be initiated or activated prior to step a), b), c). Electric cooling is initiated by supplying electric power to Peltier elements.

Compressed gas cooling can be initiated or activated prior to step a) and will be stopped prior to step b). Compressed gas cooling is initiated by purging gas through gas conduit line 1066a and/or 1066b and allowing gas to exit through throttling orifices 1068a, 1068b, or 1068c and/or through throttling orifices 1069a or 1069b, which can be in anvil, cartridge, or lower jaw.

The volumes of compartments 1030, 1034 are selected to allow fit inside or onto anvil 60a and/or lower jaw 50, with no interferences with stapling mechanisms, and are from about 1 cm$^3$ to about 20 cm$^3$, more preferably 2 to 10 cm$^3$, such as 2, 3, 5, 8, 10 cm$^3$.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A hypothermic linear surgical stapler for stapling and optionally resecting at least one tissue comprising:
    a body, a shaft assembly, and an end effector, wherein the end effector comprises a lower jaw configured to receive a staple cartridge, an anvil pivotable toward and away from the lower jaw, and a translatable knife member;
    said staple cartridge installed in the lower jaw and is disposable, said cartridge containing a plurality of deployable staples in arrays separated by a tissue resection channel through which the knife member can translate;
    said anvil having on a tissue facing surface a plurality of staple forming pockets aligned with said deployable staples;
    wherein the linear stapler comprises at least one cooled zone comprising an enclosed reservoir filled with a coolant, said reservoir located inside the anvil,
    wherein said coolant comprises an instant coolant providing cooling using an endothermic reaction.

2. The hypothermic surgical stapler of claim 1, wherein the cooled zone has a temperature from −10° C. to +10° C. prior to stapling.

3. The hypothermic surgical stapler of claim 1, wherein said coolant is comprising water, normal saline, any aqueous solution, alcohol, glycerol, ethylene glycol or mixtures thereof.

4. The hypothermic surgical stapler of claim 1, further comprising a probe configured to indicate temperature of said cooled zone.

5. The hypothermic surgical stapler of claim 1, wherein said coolant is a combination of a frozen coolant and a melted coolant.

6. The hypothermic surgical stapler of claim 1, wherein said coolant is comprising a glycerol-water mixture having melting point above 0° C. but below 8° C.

7. The hypothermic surgical stapler of claim 1, wherein a thermally conductive zone extends from being in contact with the reservoir towards the anvil tissue facing surface.

8. The hypothermic surgical stapler of claim 1, wherein the reservoir has at least one window.

\* \* \* \* \*